(12) United States Patent
Gill et al.

(10) Patent No.: US 11,980,472 B2
(45) Date of Patent: May 14, 2024

(54) SYSTEM FOR VERIFYING A PATHOLOGIC EPISODE USING AN ACCELEROMETER

(71) Applicant: Pacesetter, Inc., Sylmar, CA (US)

(72) Inventors: Jong Gill, Valencia, CA (US); Kyungmoo Ryu, Palmdale, CA (US); Fady Dawoud, Studio City, CA (US)

(73) Assignee: Pacesetter, Inc., Sylmar, CA (US)

( * ) Notice: Subject to any disclaimer, the term of this patent is extended or adjusted under 35 U.S.C. 154(b) by 222 days.

(21) Appl. No.: 17/192,961

(22) Filed: Mar. 5, 2021

(65) Prior Publication Data

US 2021/0345935 A1    Nov. 11, 2021

Related U.S. Application Data

(60) Provisional application No. 63/139,304, filed on Jan. 19, 2021, provisional application No. 63/021,778, filed on May 8, 2020.

(51) Int. Cl.
| | |
|---|---|
| *A61B 5/36* | (2021.01) |
| *A61B 5/00* | (2006.01) |
| *A61B 5/11* | (2006.01) |
| *A61B 5/361* | (2021.01) |
| *A61B 5/363* | (2021.01) |

(52) U.S. Cl.
CPC .......... *A61B 5/363* (2021.01); *A61B 5/0006* (2013.01); *A61B 5/1117* (2013.01); *A61B 5/361* (2021.01); *A61B 5/4836* (2013.01); *A61B 5/686* (2013.01); *A61B 2562/0219* (2013.01)

(58) Field of Classification Search
None
See application file for complete search history.

(56) References Cited

U.S. PATENT DOCUMENTS

| | | |
|---|---|---|
| 6,044,297 A | 3/2000 | Sheldon et al. |
| 6,102,874 A | 8/2000 | Stone et al. |
| 6,658,292 B2 | 12/2003 | Kroll et al. |
| 6,751,503 B1 | 6/2004 | Kroll |
| 8,005,543 B2 | 8/2011 | Libbus et al. |
| 8,108,035 B1 | 1/2012 | Bharmi |

(Continued)

FOREIGN PATENT DOCUMENTS

| | | |
|---|---|---|
| EP | 1331022 A2 | 7/2003 |
| WO | 2007111728 A2 | 10/2007 |

OTHER PUBLICATIONS

Extended European Search Report for corresponding EP Application No. 21156178.2-1122 dated Dec. 7, 2021 (9 pages).

*Primary Examiner* — Ankit D Tejani
(74) *Attorney, Agent, or Firm* — Dean D. Small; The Small Patent Law Group, LLC

(57) ABSTRACT

A system for verifying a candidate pathologic episode of a patient is provided. The system includes an accelerometer configured to be implanted in the patient, the accelerometer configured to obtain accelerometer data along at least one axis. The system also includes a memory configured to store program instructions and one or more processors. When executing the program instructions, the one or more processors are configured to obtain a biological signal and identify a candidate pathologic episode based on the biological signal, analyze the accelerometer data to identify a physical action experienced by the patient, and verify the candidate pathologic episode based on the physical action.

17 Claims, 14 Drawing Sheets

(56) References Cited

U.S. PATENT DOCUMENTS

| | | |
|---|---|---|
| 8,308,661 B2 | 11/2012 | Miesel et al. |
| 8,475,387 B2 | 7/2013 | Derchak et al. |
| 8,684,922 B2 | 4/2014 | Tran |
| 9,642,537 B2 | 5/2017 | Felix et al. |
| 10,124,172 B2 | 11/2018 | Lyons et al. |
| 10,610,132 B2 | 4/2020 | Gunderson et al. |
| 2006/0214806 A1* | 9/2006 | Clifford ................. A61B 5/002 340/573.1 |
| 2008/0081958 A1 | 4/2008 | Denison et al. |
| 2010/0228103 A1* | 9/2010 | Schecter .............. A61B 5/4094 600/301 |
| 2018/0325466 A1 | 11/2018 | An et al. |
| 2019/0008384 A1 | 1/2019 | Brisben et al. |
| 2021/0275023 A1* | 9/2021 | Kalantarian ........... G06N 20/00 |

\* cited by examiner

SYSTEM FOR VERIFYING A PATHOLOGIC EPISODE USING AN ACCELEROMETER

RELATED APPLICATION

The present application claims priority to U.S. Provisional Application No. 63/021,778, Titled "SYSTEM FOR VERIFYING A PATHOLOGIC EPISODE USING AN ACCELEROMETER" which was filed on 8 May 2020; and also claims priority to U.S. Provisional Application No. 63/139,304, Titled "SYSTEM FOR VERIFYING A PATHOLOGIC EPISODE USING AN ACCELEROMETER" which was filed on 19 Jan. 2021, the complete subject matter of each are expressly incorporated herein by reference in their entirety.

BACKGROUND

Embodiments herein generally relate to a method of detecting a pathologic episode by using an accelerometer implanted within a patient.

A three-dimensional (3-D) accelerometer that is implanted in a patient may detect movement of the patient during day to day activities. For example, an accelerometer may be part of an implantable cardiac monitor (ICM) or within another similar implantable medical device (IMD) to detect rotation based on the position and/or orientation of the ICM. Still, often accelerometers may be underutilized when used within an IMD.

ICMs may be used to monitor a patient for real-time pathologic episodes such as syncope. Syncope is a pause in cardiac activity that causes a patient to pass out, or lose consciousness. Syncope detection relies on the absence of R wave sensing. However, syncope detection in current ICM can be inappropriate, or inaccurate, because under-sensing of an attenuated EGM signal is diagnosed as a syncope when the patient is not experiencing a syncope.

BRIEF SUMMARY

In accordance with embodiments herein, a system for verifying a candidate pathologic episode of a patient is provided. The system includes an accelerometer configured to be implanted in the patient, the accelerometer configured to obtain accelerometer data along at least one axis. The system also includes a memory configured to store program instructions and one or more processors. When executing the program instructions, the one or more processors are configured to obtain a biological signal and identify a candidate pathologic episode based on the biological signal, analyze the accelerometer data to identify a physical action experienced by the patient, and verify the candidate pathologic episode based on the physical action.

Optionally, the physical action is activity of the patient or change in position of the patient. In one aspect, the one or more processors are further configured to reject the candidate pathologic episode as a false episode when the physical action does not correspond to the candidate pathologic episode. In another aspect, the biological signal corresponds to a cardiac activity signal, and the candidate pathologic episode is at least one of a heart failure, stroke, syncope, arrythmia, heart attack, brady event, asystole, ventricular fibrillation, ventricular tachycardia, or seizure.

Optionally, the system also includes a monitoring device configured to be implanted in the patient and in communication with the accelerometer. The monitoring device is configured to obtain the biological signal. In another aspect, the one or more processors are further configured to store the candidate pathologic episode as an actual episode, or a false episode based on the physical action analyzed. In another aspect, the monitoring device is further configured to wirelessly transmit, to an external device, at least one of the accelerometer data, or an alert signal.

Optionally, responsive to identifying the candidate pathologic episode, the one or more processors obtains the accelerometer data for an interval associated with the candidate pathologic episode. In one example, the biological signal is an accelerometer signal, and the candidate pathologic episode identified is a syncopal event.

In accordance with embodiments herein, a computer implemented method for verifying a candidate pathologic episode of a patient is provided. The method includes obtaining a biological signal and identifying a candidate pathologic episode based on the biological signal, obtaining and analyzing accelerometer data to identify a physical action experienced by the patient, and verifying the candidate pathologic episode based on the physical action.

Optionally, the method also includes denying the candidate pathologic episode as a false episode when the physical action does not correspond to the candidate pathologic episode. In another aspect, the method includes wireless transmitting, to an external device, at least one of the accelerometer data, or an alert signal. In one example, responsive to identifying the candidate pathologic episode, obtaining the accelerometer data for an interval associated with the candidate pathologic episode.

In accordance with embodiments herein, a system for monitoring a physical action of a patient is provided. The system includes an accelerometer configured to be implanted in the patient, the accelerometer configured obtain accelerometer data along at least one axis. The system also includes a memory configured to store program instructions, and one or more processors. When executing the program instructions, the one or more processors are configured to analyze the accelerometer data to identify a physical action experienced by the patient, and declare a fall-episode based on the physical action.

Optionally, the one or more processors are further configured to obtain a biological signal and identify a candidate pathologic episode based on the biological signal analyze the accelerometer data to identify a physical action experienced by the patient related to the candidate pathologic episode, and verify the candidate pathologic episode based on the physical action. In one aspect, the one or more processors are further configured to obtain accelerometer data during an interval related to the candidate pathologic episode, and analyze the accelerometer data during the interval to identify the physical action experienced by the patient related to the candidate pathologic episode. In another aspect, the physical action is at least one of activity of the patient or change in position of the patient.

Optionally, the one or more processors are further configured to communicate, to an external device, an alert signal. In one aspect, the one or more processors are further configured to communicate an activity level with the alert signal. In another aspect, the one or more processors are further configured to diagnose a syncope based on the accelerometer data obtained.

In accordance with embodiments herein, a computer implemented method for monitoring a physical action of a patient is provided. The method includes obtaining accelerometer data along at least one axis of an accelerometer, analyzing the accelerometer data to identify a physical action experienced by the patient, and declaring a fall-episode based on the physical action.

Optionally, the method also includes obtaining a biological signal and identify a candidate pathologic episode based on the biological signal, analyzing accelerometer data to identify a physical action experienced by the patient related to the candidate pathologic episode, and verify the candidate pathologic episode based on the physical action. In one aspect, the method also includes obtaining the accelerometer data during an interval related to the candidate pathologic episode, and analyzing the accelerometer data during the interval to identify the physical action experienced by the patient related to the candidate pathologic episode. In another aspect, the physical action is activity of the patient or change in position of the patient. In one example, the method includes communicating, to an external device, an alert signal.

In accordance with embodiments herein, a computer implemented method is provided for diagnosing a pathologic episode of a patient. The method includes obtaining, from a biological sensor, a biological signal, and obtaining, from an accelerometer, accelerometer data at a first rate. The method also includes analyzing the accelerometer data at the first rate to identify a physical action experienced by the patient, and analyzing the biological signal and the physical action to diagnose a pathologic episode.

Optionally, the method also includes triggering obtaining the accelerometer data at a second rate that is faster than the first rate in response to obtaining the biological signal. In one aspect, obtaining the biological signal includes obtaining accelerometer data from the accelerometer at the first rate before obtaining the biological signal, and obtaining accelerometer data from the accelerometer at a second rate after obtaining the biological signal. Obtaining the biological signal also includes comparing the accelerometer data from before obtaining the biological signal to the accelerometer data from after obtaining the biological signal. In another aspect, the second rate is faster than the first rate. In another embodiment, the second rate is based on obtaining the biological signal. In one example, obtaining accelerometer data includes obtaining accelerometer signals from more than one axis. In another example, the method also includes diagnosing one of a syncope or arrythmia, based on the analysis of the accelerometer data and the biological signal.

DETAILED DESCRIPTION

Figure 1:
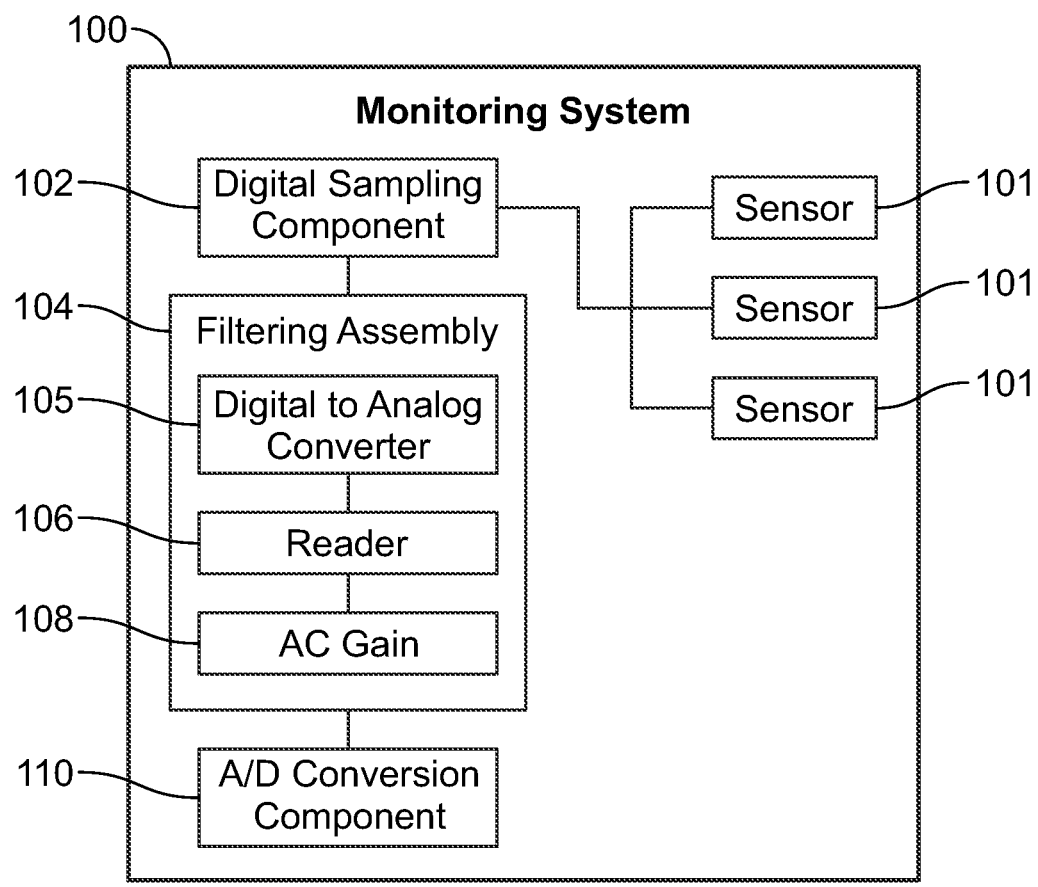
FIG. 1 illustrates a block diagram of an accelerometer formed in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

The terms "abnormal," or "arrhythmic" are used to refer to events, features, and characteristics of, or appropriate to, an unhealthy or abnormal functioning of the heart.

The terms "beat" and "cardiac event" are used interchangeably and refer to both normal and/or abnormal events.

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes.

The term "BNP" shall mean a brain natriuretic peptide. The BNP is determined from a blood test that measures levels of a protein called BPN that is made by the heart and blood vessels. A level for the BNP increases above normal when an individual experiences heart failure.

The term "body generated analyte" shall mean a test substance or specimen that is naturally generated by or naturally present in a human body. The test substance or specimen may be in liquid form (e.g., blood or other bodily fluid), solid form (e.g., tissue, fat, muscle, bone, or other organ-based material), gas form, cellular form or otherwise. Non-limiting examples of body generated analytes include hematocrit, troponin, CKMB, BNP, beta human chorionic gonadotropin (bHCG), carbon dioxide partial pressure ($pCO.sub.2$), partial pressure oxygen ($pO.sub.2$), pH, PT, ACT, activated partial thromboplastin time (APTT), sodium, potassium, chloride, calcium, urea, glucose, creatinine, lactate, oxygen, and carbon dioxide, thyroid stimulating hormone, parathyroid hormone, D-dimer, prostate specific antibody, TCO2, Anion Gap, ionized calcium, urea nitrogen, lactose, hemoglobin, pH, PCO2, PO2, HCO3, Base Excess, O2, ACT Kaolin, ACT Celite, PT/INR, ?-hCG, cTnI, CK-MB, BNP and the like, and combinations thereof. The analyte may be tested in a liquid sample that is whole blood, however other samples can be used including blood, serum, plasma, urine, cerebrospinal fluid, saliva and amended forms thereof. Amendments can include diluents and reagents such as anticoagulants and the like.

The terms "body generated analyte-based index" and "BGA index" shall mean an index that is calculated based on one or more body generated analytes, where the index is indicative of a state of one or more pathologic or physiologic characteristics of interest (COI) of the patient. As non-limiting examples, the pathologic or physiologic COI may relate to diuretic response, CRS, intravascular volume depletion/overload, total body overload, malnutrition, peripheral edema, adenomatous GI tract absorption, liver congestion, liver protein generation state, hypoglycemic, hyperglycemic and the like.

The term "IMD" shall mean an implantable medical device. Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker, and the like. The IMD may measure electrical and/or mechanical information. For example, the IMD may include one or more structural and/or functional aspects of the device(s) described in U.S. Pat. No. 9,333,351, entitled "NEUROSTIMULATION METHOD AND SYSTEM TO TREAT APNEA" issued May 10, 2016 and U.S. Pat. No. 9,044,610, entitled "SYSTEM AND METHODS FOR PROVIDING A DISTRIBUTED VIRTUAL STIMULATION CATHODE FOR USE WITH AN IMPLANTABLE NEUROSTIMULATION SYSTEM" issued Jun. 2, 2015, which are hereby incorporated by reference. The IMD may monitor transthoracic impedance, such as implemented by the CorVue algorithm offered by St. Jude Medical. Additionally or alternatively, the IMD may include one or more structural and/or functional aspects of the device(s) described in U.S. Pat. No. 9,216,285, entitled "LEADLESS IMPLANTABLE MEDICAL DEVICE HAVING REMOVABLE AND FIXED COMPONENTS" issued Dec. 22, 2015 and U.S. Pat. No. 8,831,747, entitled "LEADLESS NEUROSTIMULATION DEVICE AND METHOD INCLUDING THE SAME" issued Sep. 9, 2014, which are hereby incorporated by reference. Additionally or alternatively, the IMD may include one or more structural and/or functional aspects of the device(s) described in U.S. Pat. No. 8,391,980, entitled "METHOD AND SYSTEM FOR IDENTIFYING A POTENTIAL LEAD FAILURE IN AN IMPLANTABLE MEDICAL DEVICE" issued Mar. 5, 2013 and U.S. Pat. No. 9,232,485, entitled "SYSTEM AND METHOD FOR SELECTIVELY COMMUNICATING WITH AN IMPLANTABLE MEDICAL DEVICE" issued Jan. 5, 2016, which are hereby incorporated by reference. Additionally or alternatively, the IMD may be a subcutaneous IMD that includes one or more structural and/or functional aspects of the device(s) described in U.S. application Ser. No. 15/973,195, entitled "SUBCUTANEOUS IMPLANTATION MEDICAL DEVICE WITH MULTIPLE PARASTERNAL-ANTERIOR ELECTRODES" filed May 7, 2018; U.S. application Ser. No. 15/973,219, entitled "IMPLANTABLE MEDICAL SYSTEMS AND METHODS INCLUDING PULSE GENERATORS AND LEADS" filed May 7, 2018; U.S. application Ser. No. 15/973,249, entitled "SINGLE SITE IMPLANTATION METHODS FOR MEDICAL DEVICES HAVING MULTIPLE LEADS", filed May 7, 2018, which are hereby incorporated by reference in their entireties. Further, one or more combinations of IMDs may be utilized from the above incorporated patents and applications in accordance with embodiments herein. Embodiments may be implemented in connection with one or more subcutaneous implantable medical devices (S-IMDs). For example, the S-IMD may include one or more structural and/or functional aspects of the device(s) described in U.S. application Ser. No. 15/973,219, entitled "IMPLANTABLE MEDICAL SYSTEMS AND METHODS INCLUDING PULSE GENERATORS AND LEADS", filed May 7, 2018; U.S. application Ser. No. 15/973,195, entitled "SUBCUTANEOUS IMPLANTATION MEDICAL DEVICE WITH MULTIPLE PARASTERNAL-ANTERIOR ELECTRODES", filed May 7, 2018; which are hereby incorporated by reference in their entireties. The IMD may represent a passive device that utilizes an external power source, and entirely mechanical plan will device, and/or an active device that includes an internal power source. The IMD may deliver some type of therapy/treatment, provide mechanical circulatory support, and/or merely monitor one or more physiologic characteristics of interest (e.g., PAP, CA signals, impedance, heart sounds).

Additionally or alternatively, embodiments herein may be implemented in connection with an integrated healthcare patient management system or network, such as described in "METHODS, DEVICE AND SYSTEMS FOR HOLISTIC INTEGRATED HEALTHCARE PATIENT MANAGEMENT", provisional application 62/875,870, filed Jul. 18, 2019, which is incorporated by reference herein in its entirety.

Additionally or alternatively, embodiments herein may be implemented in connection with the methods and systems described in "METHOD AND SYSTEM FOR HEART CONDITION DETECTION USING AN ACCELEROMETER", Provisional Application No. 63/021,775, which is incorporated by reference herein in its entirety.

Additionally or alternatively, embodiments herein may be implemented in connection with the methods and systems described in "METHOD AND DEVICE FOR DETECTING RESPIRATION ANOMALY FROM LOW FREQUENCY COMPONENT OF ELECTRICAL CARDIAC ACTIVITY SIGNALS", U.S. application Ser. No. 16/869,733, filed on the same day as the present application, which is incorporated by reference herein in its entirety.

Additionally or alternatively, the IMD may represent or operate in conjunction with a body generated analyte test device or "BGA test device" which represents any and all equipment, devices, disposable products utilized to collect and analyze a BGA. The IMD may implement one or more of the methods, devices and systems described in the following publications, all of which are incorporated herein by reference in their entireties: U.S. Pat. No. 8,514,086, entitled "DISPLAYS FOR A MEDICAL DEVICE", issued Aug. 20, 2013; U.S. Patent Publication No. 2011/0256024, entitled "MODULAR ANALYTE MONITORING DEVICE", published Oct. 20, 2011; U.S. Patent Publication No. 2010/0198142, entitled "MULTIFUNCTION ANALYTE TEST DEVICE AND METHODS THEREFORE", published Aug. 5, 2010; U.S. Patent Publication No. 2011/0160544, entitled "SYSTEM AND METHOD FOR ANALYSIS OF MEDICAL DATA TO ENCOURAGE HEALTHCARE MANAGEMENT", published Jun. 30, 2011; U.S. Pat. No. 5,294,404, entitled "REAGENT PACK FOR IMMUNOASSAYS" issued Mar. 15, 1994; U.S. Pat. No. 5,063,081, entitled "METHOD OF MANUFACTURING A PLURALITY OF UNIFORM MICROFABRICATED SENSING DEVICES HAVING AN IMMOBILIZED LIGAND RECEPTOR" issued Nov. 5, 1991; U.S. Pat. No. 7,419,821, entitled "APPARATUS AND METHODS FOR ANALYTE MEASUREMENT AND IMMUNOASSAY" issued Sep. 2, 2008; U.S. Patent Publication No. 2004/0018577, entitled "MULTIPLE HYBRID IMMUNOASSAYS" published Jan. 29, 2004; U.S. Pat. No. 7,682,833, entitled "IMMUNOASSAY DEVICE WITH IMPROVED SAMPLE CLOSURE" issued Mar. 23, 2010; U.S. Pat. No. 7,723,099, entitled "IMMUNOASSAY DEVICE WITH IMMUNO-REFERENCE ELECTRODE" issued May 25, 2010; and Baj-Rossi et al. "FABRICATION AND PACKAGING OF A FULLY IMPLANTABLE BIOSENSOR ARRAY", (2013) IEEE, pages 166-169, which are hereby incorporated by reference in their entireties.

The term "obtains" and "obtaining", as used in connection with data, signals, information and the like, include at least one of i) accessing memory of an external device or remote server where the data, signals, information, etc. are stored, ii) receiving the data, signals, information, etc. over a wireless communications link between the ICM and a local external device, and/or iii) receiving the data, signals, information, etc. at a remote server over a network connection. The obtaining operation, when from the perspective of an ICM, may include sensing new signals in real time, and/or accessing memory to read stored data, signals, information, etc. from memory within the ICM. The obtaining operation, when from the perspective of a local external device, includes receiving the data, signals, information, etc. at a transceiver of the local external device where the data, signals, information, etc. are communicated from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

The terms "processor," "a processor", "one or more processors" and "the processor" shall mean one or more processors. The one or more processors may be implemented by one, or by a combination of more than one implantable medical device, a wearable device, a local device, a remote device, a server computing device, a network of server computing devices and the like. The one or more processors may be implemented at a common location or at distributed locations. The one or more processors may implement the various operations described herein in a serial or parallel manner, in a shared-resource configuration and the like.

FIG. 1 illustrates a schematic diagram of a monitoring system 100. In one example, the monitoring system is or includes an accelerometer. In one embodiment when the monitoring system 100 is an accelerometer, the accelerometer may be a chip for placement in an IMD. In another embodiment, the accelerometer is formed and operates in the manner described in U.S. Pat. No. 6,937,900, titled "AC/DC Multi-Axis Accelerometer For Determining A Patient Activity And Body Position," the complete subject matter which is expressly incorporated herein by reference. In an embodiment, when the monitoring system is an accelerometer, the accelerometer includes sensors that generate first (X), second (Y) and third (Z) accelerometer signals along corresponding X, Y and Z axes (also referred to as first axis accelerometer signals, second axis accelerometer signals and third axis accelerometer signals). The X, Y and Z axes accelerometer signals collectively define a three-dimensional (3D), or multi-dimensional (MD) accelerometer data set. While examples herein are described in connection with an accelerometer that generates accelerometer signals along three orthogonal axes, it is recognized that embodiments may be implemented wherein accelerometer signals are generated along two or more axes, including more than three axes.

The monitoring system 100 may include sensors 101 that monitor and receive signals from the X, Y and Z axes. In one embodiment, the individual X, Y and Z signals are received by a digital sampling component 102 that receives a digital input. Coupled to the digital sampling component 102 is a filtering assembly 104 that may include a digital to analog converter 105 to form an alternating current (AC) signal, a reader device 106, and an AC gain device 108. While in this embodiment, the filtering assembly includes the devices provided, in other examples, other devices may be utilized to filter the digital input signal for processing.

The monitoring system 100 may also include an analog to digital conversion component 110, along with a position, or direct current (DC) component. In one example, the analog to digital conversion component may be an 8-bit analog to digital converter (ADC). The evaluation version of the monitoring system 100 may provide 3-axis (X and Y along the chip, Z normal to the chip) DC-coupled posture signal corresponding to 3 orthogonal directions as well as 3-axis AC-coupled activity signal. In one embodiment, each of the 6 signal may be sampled at 100 Hz and accumulated over 1 sec for a total of 12 signals ([X/Y/Z],[posture/activity], [100/1 Hz]). This MD accelerometer data may be used to describe embodiments herein.

While described as a digital signal in relation to FIG. 1, in other embodiments the signal may be an analog signal, filtered, amplified, etc. The accelerometer data signals may be recorded in a data storage of the accelerometer, of an IMD, of a remote device etc. Alternatively, the accelerometer data set may be collected from a remote device, or received from a storage device coupled to the accelerometer. To this end, the accelerometer data set may be a multi-dimensional accelerometer data set.

The accelerometer sensors 101 may collect accelerometer signals from two or more axes. The accelerometer signals may come from at least two of the X-axis, Y-axis, or Z-axis. In one example, the accelerometer signals may be collected from all three axes.

Figure 2A:
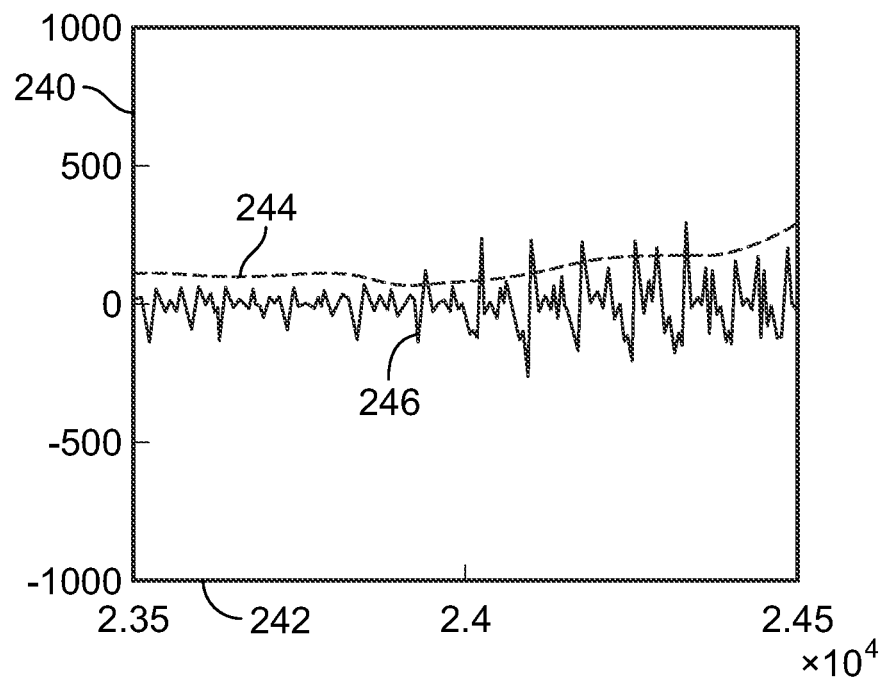
FIG. 2A illustrates a graph of activity over time in accordance with embodiments herein.
Figure 2B:
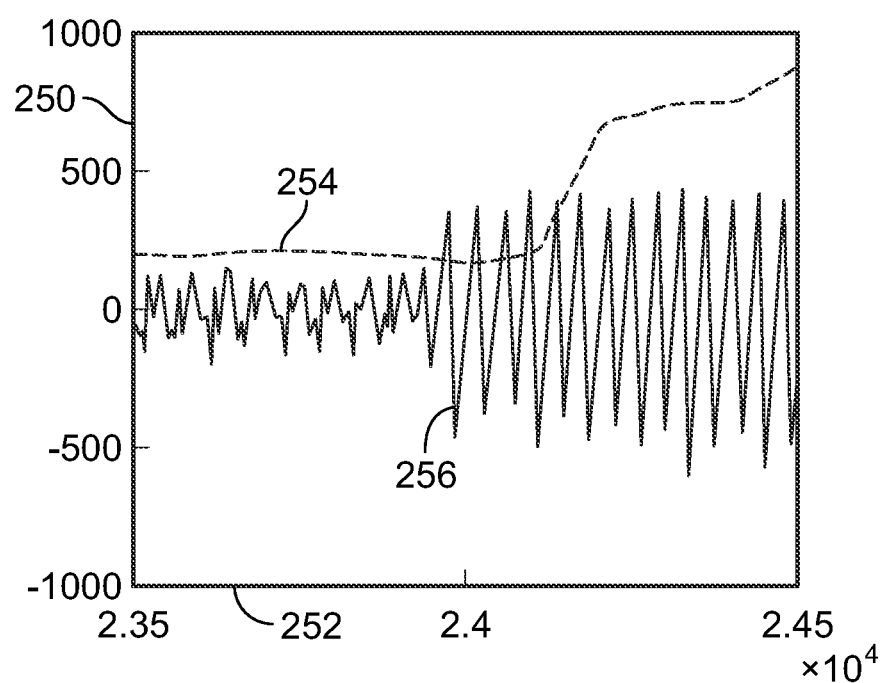
FIG. 2B illustrates a graph of activity over time in accordance with embodiments herein.
Figure 2C:
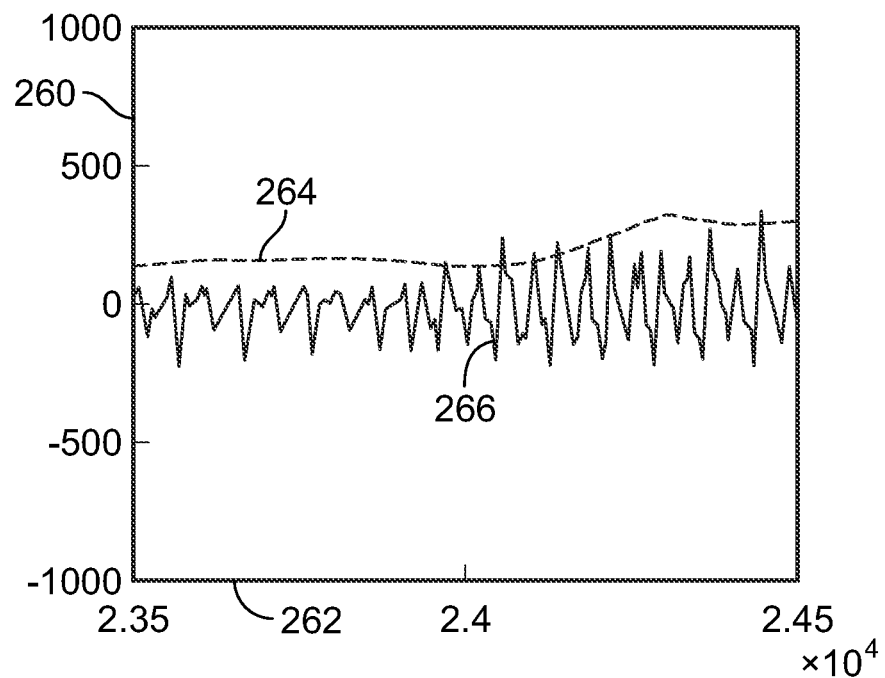
FIG. 2C illustrates a graph of activity over time in accordance with embodiments herein.

FIGS. 2A-2F illustrate example accelerometer signals that may be collected and recorded over 1 second intervals by the monitoring system 100 of FIG. 1. Specifically, IMD accelerometer signals may be collected and recorded, including both position related data sets and activity related data sets. Posture related data sets include the positions and changes in position of the patient along an X axis, Y axis, and/or Z axis. Activity related data sets include measurements related to the activity of the patient, including walking, running, sleeping, sitting up, jogging, falling, or the like. FIG. 2A illustrates an activity level of the patient 240 over time 242 for the X axis, with activity of the patient over 1 second 244 monitored, along with 100 Hz activity of the patient over 1 second 246. Similarly, FIG. 2B illustrates activity level of the patient 250 over time 252 for the Y axis, with activity over 1 second 254 monitored, along with 100 Hz activity over 1 second 256. FIG. 2C meanwhile illustrates activity level of the patient 260 over time 262 for the Z axis, with activity level of the patient over 1 second 264 monitored, along with 100 Hz activity over 1 second 266.

Figure 2D:
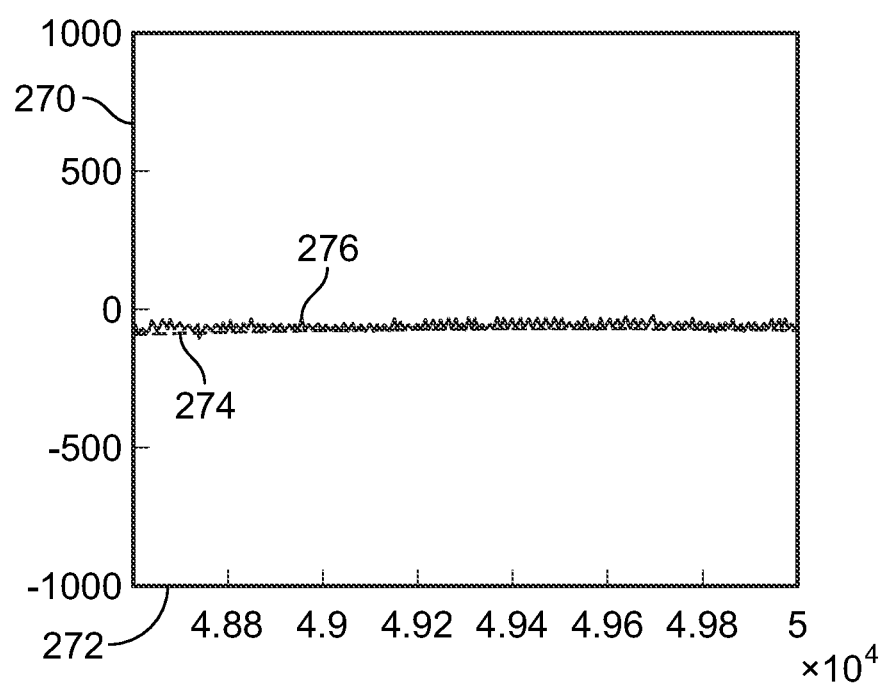
FIG. 2D illustrates a graph of position over time in accordance with embodiments herein.
Figure 2E:
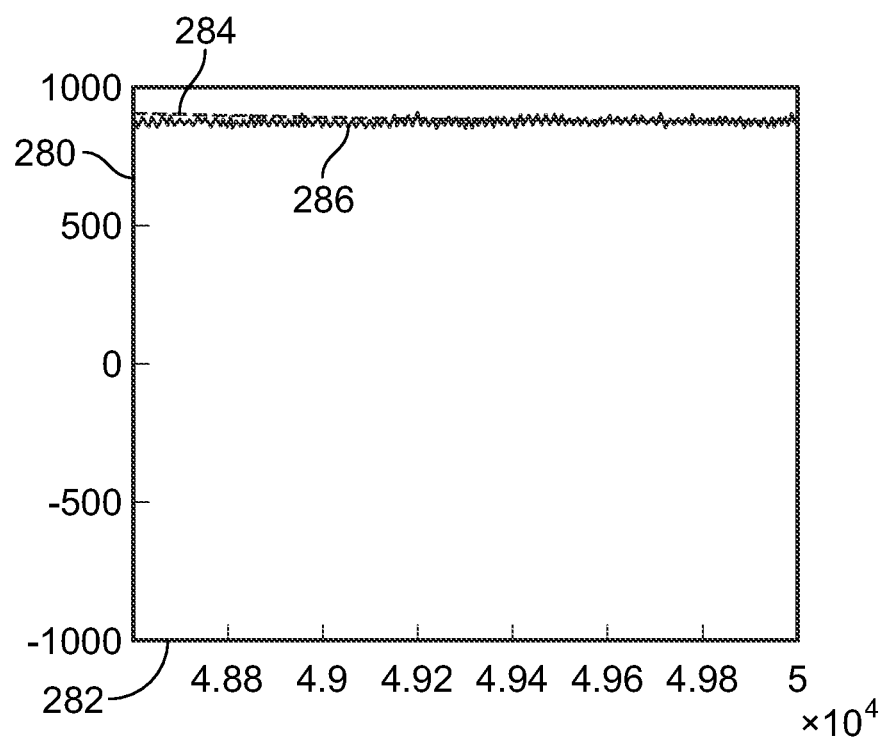
FIG. 2E illustrates a graph of position over time in accordance with embodiments herein.
Figure 2F:
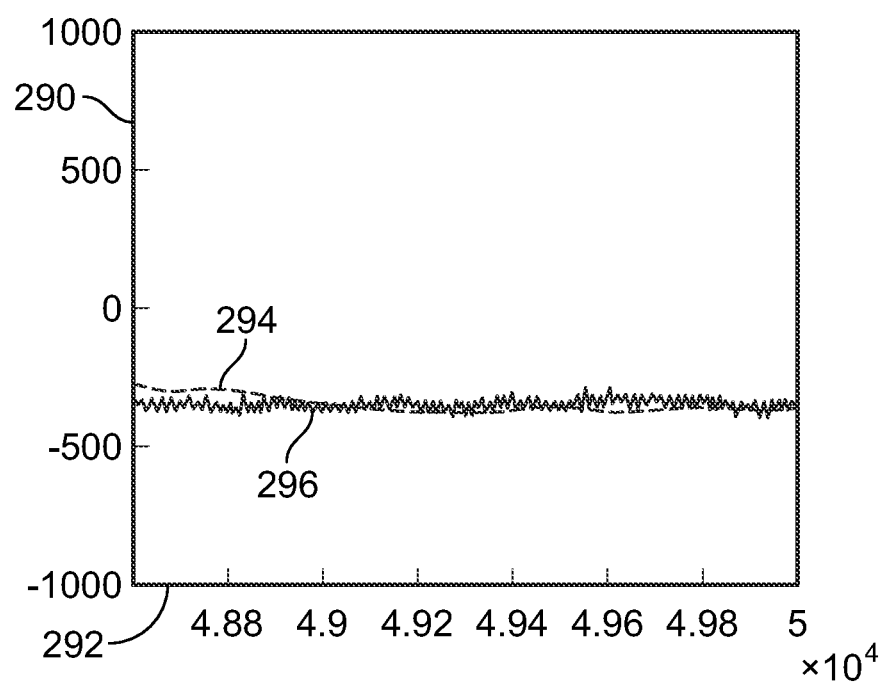
FIG. 2F illustrates a graph of position over time in accordance with embodiments herein.

In addition, or alternatively, as illustrated in FIGS. 2D-2F, posture may be monitored and recorded, including posture position 270 over time 272 for the X axis, wherein posture position over 1 second 274 along the X axis may be monitored along with posture position for 100 Hz over 1 second 276. Similarly, FIG. 2G shows posture position 280 over time 282 for the Y axis, including posture position over 1 second 284 along the Y axis along with posture position for 100 Hz over 1 second 286. Finally, for the Z axis, FIG. 2F illustrates posture position 290 over time 292, including posture position over 1 second 294 along with posture position for 100 Hz over 1 second 296.

Additionally or alternatively, in accordance with embodiments herein, the accelerometer signals and posture positions may be utilized to detect various types of erratic physical actions. Nonlimiting examples of erratic physical actions include seizures or another erratic episode experienced by the patient. For example, when a diabetic patient experiences unduly low blood sugar, the diabetic patient may experience various types of seizures. As another example, epileptic patients may experience various types of seizures or undergo other erratic physical actions. The accelerometer signals and changes in posture may be analyzed for patterns associated with such erratic physical actions, such as patterns associated with various types of seizures. For example, the erratic physical action may involve the patient falling and uncontrollably shaking while in a supine position. Another example of an erratic physical action may involve a patient standing, sitting or maintaining some other position while convulsively shaking. As yet another example, with other types of seizure related disorders, a patient may repeatedly and uncontrollably move one or more limbs in a back-and-forth motion. The erratic physical actions may be identified through accelerometer signals and posture positions. For example, templates may be developed for a patient population or for an individual patient where the templates for the X, Y and Z axes of the accelerometer signals correspond to a particular erratic physical action. Additionally or alternatively, the X, Y and Z accelerometer signals may be analyzed for other patterns known to be present during certain seizures, such as a repetitive motion in a particular direction that maintains a relatively constant frequency and/or amplitude.

Figure 3A:
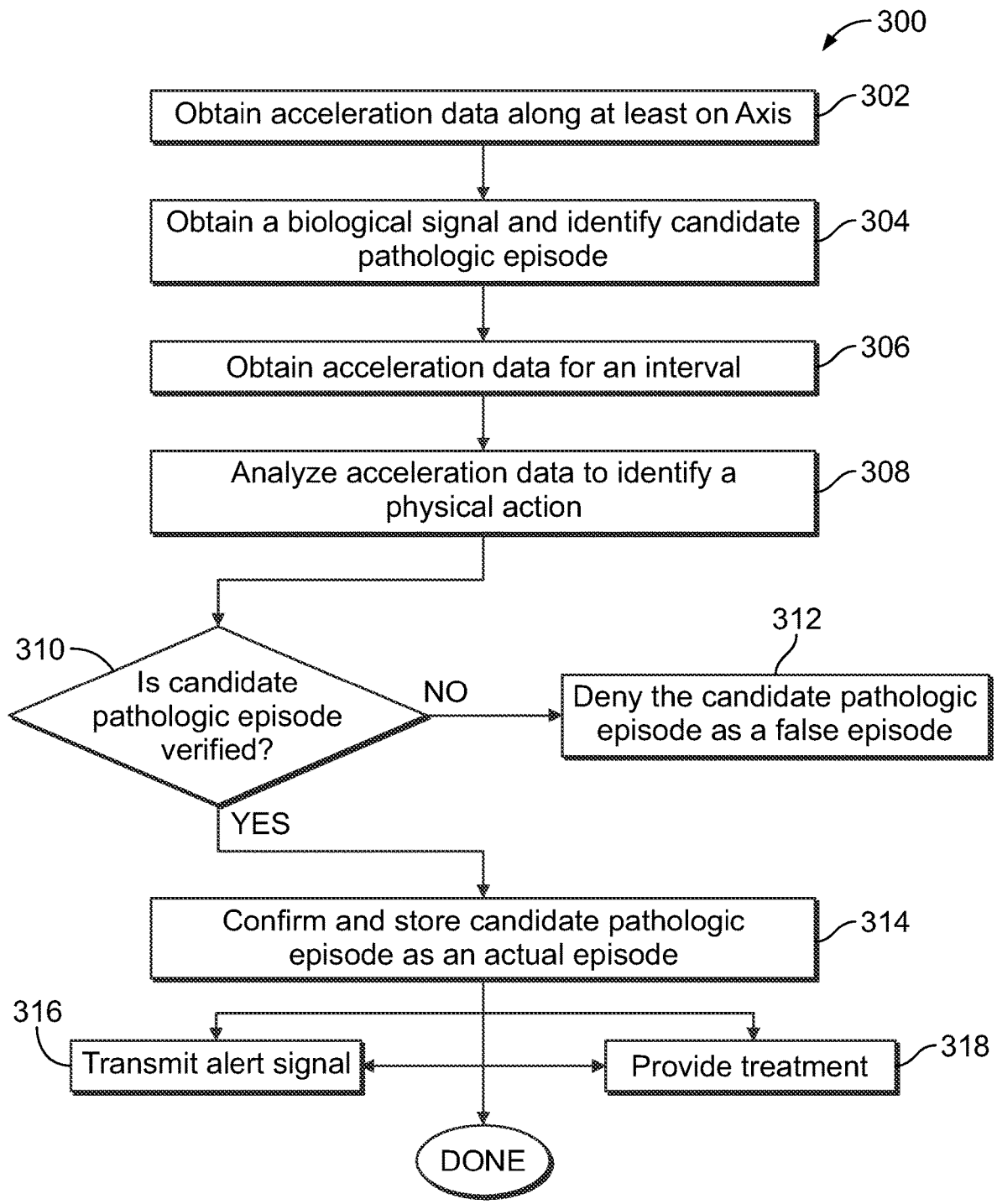
FIG. 3A illustrates a flow block diagram of a method of verifying a diagnosis in accordance with embodiments herein.

FIG. 3A illustrates a flow block diagram of a method 300 of verifying a candidate pathologic episode of a patient and taking remedial actions in response to verifying such a candidate pathologic episode. In one example the monitoring system used to perform the method includes an accelerometer, similar to that illustrated in FIG. 1. By monitoring the physical actions of a patient using an accelerometer, potentially adverse pathologic episodes, or conditions may be confirmed.

Non-limiting examples of candidate pathologic episodes include heart failure, stroke, syncope, arrythmia, heart attack, asystole, brady event, neurological episodes, ventricular fibrillation (VF), ventricular tachycardia (VT), a diabetic seizure, and epileptic seizure, or any other type of seizure, episodes that may result from substantial reduction or change in pulmonary arterial pressure and the like. Specifically, to reduce a false detection of a pathologic episode, such as a syncope, accelerometer data may be used to verify the detection of the pathologic episode. Alternatively, the monitoring system may be used in general to track a patient and detect a fall-episode, even without a pathologic episode occurring. In this manner, the accelerometer may serve dual purposes in both detecting falls, and confirming pathologic episodes.

At 302, an accelerometer obtains accelerometer data along at least one axis. The accelerometer data may include IMD accelerometer data, activity related data, posture related data, or the like. The IMD accelerometer data may be obtained from any of the three axes in any manner described herein. The posture related data of the accelerometer may similarly be obtained from any axis or may be a composite of the axes. The accelerometer may be programed to obtain the accelerometer data continuously, during intervals when increase activity of the patient is determined, or the like. The intervals may be at nighttime, during an exercise program, during portions of a day, etc.

At 304, a monitoring device operates to obtain a biological signal and identify a candidate pathologic episode based on the biological signal. In one embodiment, the monitoring device is an IMD. In one embodiment, the IMD is an ICM that monitors cardiac activity signals of the heart for arrythmias (e.g., heart attacks, VFs, VTs, syncope, etc.). Additionally or alternatively, the IMD may be a BGA device, such as described in the '870 Provisional Application. The biological signal may be any signal that provides information about pathologic condition of a patient, including acceleration signals, cardiac activity signals, heart sound signals, impedance signals, pulmonary arterial pressure signals, signals indicative of a diabetic seizure, signals indicative of an epileptic seizure, or signals indicative of any other type of seizure and the like. Specifically, the biological signal may be used by a monitoring device, such as an ICM, a BGA device, PAP sensor or otherwise to detect a pathologic episode.

Additionally or alternatively, the identification at 304 may include applying an application specific model to calculate a health risk index, such as described in the '870 Provisional Application. When the health risk index exceeds a threshold, the process may declare a candidate pathologic episode to exist. In one example, the MD acceleration data is utilized to diagnose a syncope. In particular, diagnosis of a syncope, or other pathologic episode is exemplary of identifying a candidate pathologic episode.

At 306, responsive to identifying the candidate pathologic episode, the one or more processors obtains accelerometer data for an interval associated with the candidate pathologic episode. In one example the interval is for the accelerometer data received over the previous minute. In another example, the interval is for thirty seconds. In yet another example the interval is in a range between one second and five minutes. In another embodiment, the command signal may initiate the interval, and the interval may last a determined amount of time and include the time window pre/post the candidate pathologic episode.

At 308, the one or more processors analyze the obtained accelerometer data for the interval associated with the candidate pathologic episode to identify a physical action experienced by the patient. In some instances, an IMD may detect a false episode, or indication a pathologic episode is present, when no such pathologic episode is occurring. Based on the nature of the pathologic episode, an accelerometer is expected to provide measurements that are indicative of a physical action experienced by the patient during the time when the pathologic episode is detected, where the interval associated with the candidate pathologic episode incudes the time when the pathologic episode is detected. For instance, during a syncopal event, a patient loses consciousness, typically falls to the ground, and all activity for the patient ceases. Therefore, an accelerometer would be able to detect that activity of the patient has ceased, or that the position of the individual has gone from standing to laying down during the interval associated with the syncope. Physical actions experienced by the patient may include the absence of activity of the patient, variation in activity of the patient, increase in sudden but transient activity associated with fall to the ground, activity of the patient decreasing below a threshold level, a patient moving from a standing to a laying down position, a patient moving from a sitting to a laying down position, a patient moving from a sitting upright to slumped position, a patient moving from sitting upright to laying on a side, etc. To this end, a monitored heart sound would not be considered a physical action experienced by a patient.

In one embodiment, accelerometer data obtained may be used to determine activity of a patient. In another embodiment, the accelerometer data received may be used to determine position of the accelerometer. In other embodiments, the accelerometer data may be used for both determining activity of a patient and accelerometer position At 310, one or more processors determine whether to verify the candidate pathologic episode based on the physical action. The determination may be made using algorithms, models, mathematical functions, look up tables, decision trees, etc. When the candidate pathologic episode is not verified, a false detection, or false episode is presented, and flow moves to 312. Alternately, if the candidate pathologic episodes are associated the physical action such as fall, additional diagnosis of fall will be added to the candidate pathologic episode. Specifically, the candidate pathologic episode is not verified when the accelerometer data indicates one or more of i) activity of a patient is present, ii) a change in activity of a patient is above a threshold, iii) a change in position has not occurred, iv) a change in position is less than a threshold change, or the like. In one embodiment, only an activity level of a patient is analyzed to verify a candidate pathologic episode, and the position of the patient is not analyzed. Alternatively, only the position of the patient is analyzed to verify a candidate pathologic episode, and activity level is not analyzed. In yet another embodiment, both activity level and position of a patient may be analyzed for verification. By having at least two separate verification steps, false readings are identified more reliably, thereby reducing incorrect diagnosis.

Additionally or alternatively, in accordance with embodiments herein, the accelerometer data may be analyzed to identify erratic physical actions (e.g. seizures). The accelerometer data may indicate changes in posture and/or repetitive movements having patterns associated with certain erratic physical actions. For example, the erratic physical action may involve the patient falling and uncontrollably shaking while in a supine position. Another example of an erratic physical action may involve a patient standing, sitting or maintaining some other position while convulsively shaking. As yet another example, with other types of seizure related disorders, a patient may repeatedly and uncontrollably move one or more limbs in a back-and-forth motion.

Additionally or alternatively, at 310, the one or more processors may compare one or more templates to the of the accelerometer data along one or more of the X, Y and Z axes (and/or a composite signal formed from a combination of X, Y and Z accelerometer data). For example, X, Y and Z templates may be developed for a patient population or for an individual patient where the templates for the X, Y and Z axes of the accelerometer signals correspond to a particular erratic physical action. Additionally or alternatively, the X, Y and Z accelerometer signals may be analyzed for other patterns known to be present during certain seizures, such as a repetitive motion in a particular direction that maintains a relatively constant frequency and/or amplitude.

At 312, the one or more processors deny the candidate pathologic episode as a false episode when the physical action does not correspond to the candidate pathologic episode. A false episode represents a candidate pathologic episode that was incorrectly detected or determined by a monitoring device. In contrast, an actual episode is provided with the candidate pathologic episode detected by a monitoring device is correct. In an example, in response to denying the candidate pathologic episode as a false episode, the IMD may communicate a "false positive" signal to a remote device or third party, wherein the false positive signal indicates that the IMD has incorrectly identified a candidate pathologic episode. Additionally, the false positive signal may be logged in a storage device or memory to track trends or otherwise monitor for a potentially faulty or malfunctioning monitoring device.

Additionally or alternatively, at 312, the one or more processors may deny the candidate pathologic episode as a false episode, and provide a communication to a remote device that no collapse was detected. The one or more processors may further communicate additional information related to the posture and/or activity signals, such as the raw acceleration signals or an indication of one or more characteristics within the acceleration signals. In such a case, an automated system or a person remote to the patient could call or contact the patient to see if the pathologic episode detected by the monitoring device was incorrect. If no response occurs from a call, then emergency services could be contacted.

When the candidate pathologic episode is verified at 310, the candidate pathologic episode is an actual episode, and flow moves to 314. At 314, the one or more processors confirm and store the candidate pathologic episode as an actual episode. As a result of the verification, greater certainty of the diagnosed pathologic episode is provided.

At 316, optionally, the monitoring device automatically communicates an alert signal in response to the verification of the actual episode. The alert signal may be communicated to a remote device, emergency services, hospital, doctor's office and/or phone, clinician office and/or phone, third party, PDE, home monitoring device, etc. The alert signal may include an auditory alarm or sound, flashing lights, or the like to bring attention to the alert signal. The monitoring device may also record the pathologic episode, accelerometer data, activity related data, posture related data, or the like resulting in the transmission of the alert signal.

At 318, optionally, the monitoring device may automatically provide treatment in response to verification of an actual episode. For example, when the monitoring device also represents an IMD configured to deliver therapy, the treatment may include pacing, shock, release of medication (e.g. insulin), etc. In this manner, the treatment may immediately be provided for the patient.

In one example, a syncopal event is diagnosed by a monitoring device as a candidate pathologic episode. In response, accelerometer data for an interval of the previous minute is obtained by the one or more processors. Based on an analysis of the accelerometer data, the activity level of a patient is not zero during the entire interval. As a result, the physical action experienced by the patient identified by the one or more processors is that of a healthy individual. Based on the physical action identified, that candidate pathologic episode is denied as a false episode, and no additional action regarding the candidate pathologic episode is undertaken by the monitoring device.

In an alternative embodiment, a VF or VT is identified by the monitoring device. In response, both an activity level and change in position of the patient is obtained from the accelerometer data for the previous two minutes. When analyzed, the activity level indicates that activity of the patient stopped fifteen seconds before the VF or VT was identified. Similarly, when analyzed, fifteen seconds before the VF or VT was identified the patient has moved from a standing position to a supine position. Therefore, the activity of the patient and position of the patient are used to verify the VT or VF is an actual episode. In an embodiment when the monitoring device is a leadless monitoring device capable of providing a shock as a treatment to the VT or VF, as a result of receiving the verification of the actual episode, anti-tachycardia pacing (ATP) is ceased, and a shock is automatically provided to the heart.

In yet another embodiment, a diabetic patient may have low blood sugar causing them to pass out or have a seizure. The monitoring device represent a BGA device. The BGA device may identify that the diabetic patients BGA data (e.g. blood sugar) indicate a potential that the patient is experiencing a seizure. In connection there with, the accelerometer data is collected and analyzed to identify posture for a desired period of time (e.g. the prior four minutes). When analyzed, the posture related data may show that the patient has moved from a standing position to a supine position, and erratic movement in the supine position is occurring. In response to verifying the seizure, an alert signal is communicated to first responders, and/or local medical personnel. In addition, automatic treatment in the form of drug delivery is activated to combat the low blood sugar. In this manner, medical personnel are contacted, while treatment is immediately provided.

In another embodiment, in addition to verifying a candidate pathologic episode, the one or more processor may also monitor the patient continuously for a fall-episode. In particular, a fall-episode is when a patient falls to the ground, and often is associated with the patient being unable to stand. During a fall-episode the position of the patient suddenly changes from standing to supine, and sometimes remains supine for an extended period of time. Based on the accelerometer data obtained at 302, when a sudden position change followed by a determined period in a supine position occurs, the one or more processors may declare a fall-episode based on the physical action, and an alert signal may be communicated as described in relation to 316. Declaring is any determination of a fall-episode and communicating of a signal to alert a third party accordingly. In this manner, the system may provide functionality as both a monitor for falling and verification of a pathologic episode.

Figure 3B:
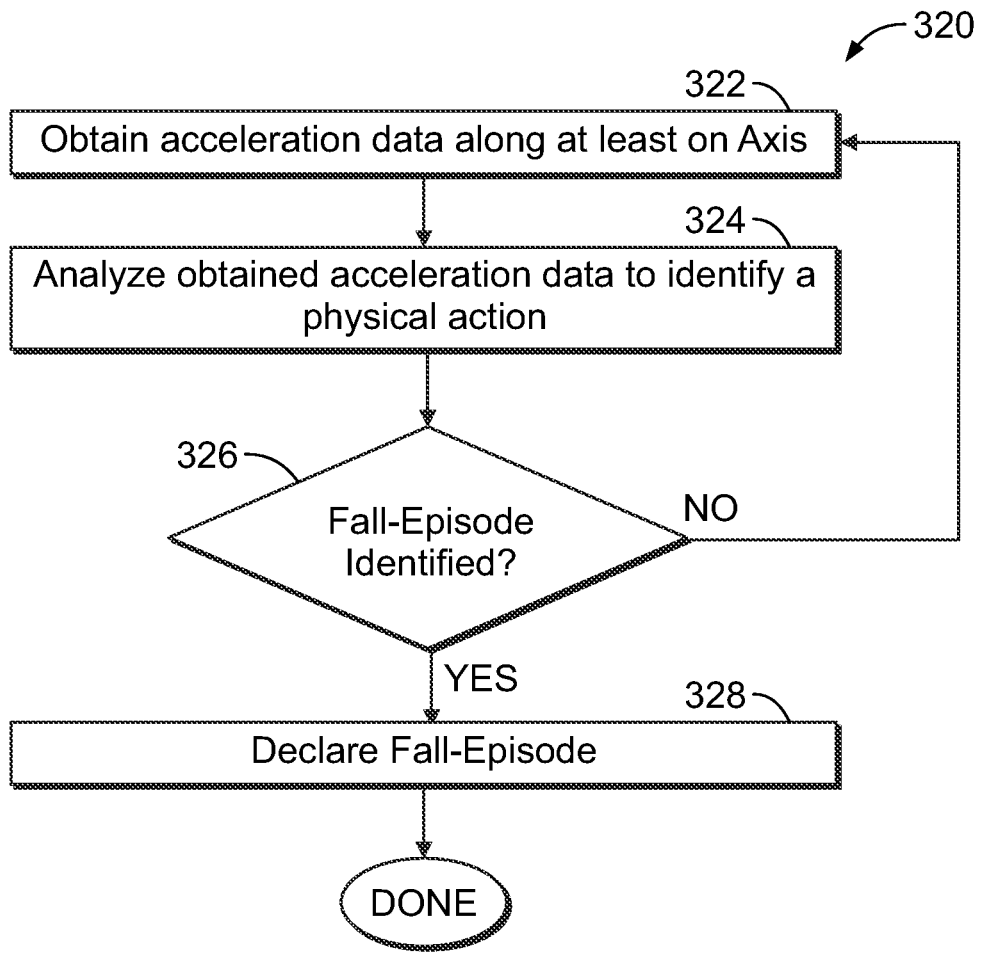
FIG. 3B illustrates a flow block diagram of a method of monitoring a physical action of a patient in accordance with embodiments herein.

While FIG. 3A illustrates an embodiment where dual functionality may be presented by a monitoring system that utilizes, or is an accelerometer, FIG. 3B illustrates a method 320 of monitoring a physical action of a patient. Specifically, the monitoring system may be used simply as a system the detects fall-episodes without verifying a pathologic episode.

At 322, an accelerometer obtains accelerometer data along at least one axis. The accelerometer data may include MD accelerometer data, activity related data, posture related data, or the like. The MD accelerometer data may be obtained from any of the three axes in any manner described herein. The posture related data of the accelerometer may similarly be obtained from any axis, or may be a composite of the axes. The accelerometer may be programed to obtain the accelerometer data continuously, during intervals when increase activity of the patient is determined, or the like. The intervals may be at nighttime, during an exercise program, during portions of a day, etc.

At 324, the one or more processors analyze the obtained accelerometer data to identify a physical action experienced by the patient. Physical actions experienced by the patient may include the absence of activity of the patient, variation in activity of the patient, presence of short-lasting large activity of the patient above a threshold level, activity of the patient decreasing below a threshold level, a patient moving from a standing to a laying down position, a patient moving from a sitting to a laying down position, a patient moving from sitting upright to laying on a side, etc. In one embodiment, accelerometer data obtained may be used to determine activity of a patient. In another embodiment, the accelerometer data received may be used to determine position of the accelerometer. In other embodiments, the accelerometer data may be used for both determining activity of a patient and accelerometer position.

At 326, a determination is made whether a fall-episode has been identified. Specifically, by analyzing the obtained accelerometer data, the physical action experienced by the patient may be a fall. The determination regarding whether the accelerometer data identifies a fall-episode may be made utilizing algorithms, models, mathematical functions, look up tables, decision trees, etc. In one embodiment MD accelerometer signals are utilized to determine an activity level of the patient to make the determination. Alternatively MD accelerometer signals are utilized to determine a change in accelerometer position to determine the fall-episode has occurred. In another embodiment, both activity level and a change in position is used to determine a fall-episode has occurred. If at 326, a fall-episode is not identified, the one or more processors continue obtaining and analyzing the accelerometer data.

If at 326, a fall-episode is identified, at 328 the one or more processors declare a fall-episode based on the physical action. As described above, declaring is any determination of a fall-episode and communicating of a signal to alert a third party accordingly. The communication may be a wireless transmit, over a wire, over the air, through the cloud, electronic, or the like. The third party may be a clinician, family member, hospital, neighbor, or the like. In one embodiment, an alert signal is communicated that may include an auditory alarm, visual alarm, text message, electronic message, etc. that alerts another of the fall-episode. In this manner, the monitoring system may be utilized as a fall-episode detector.

Figure 3C:
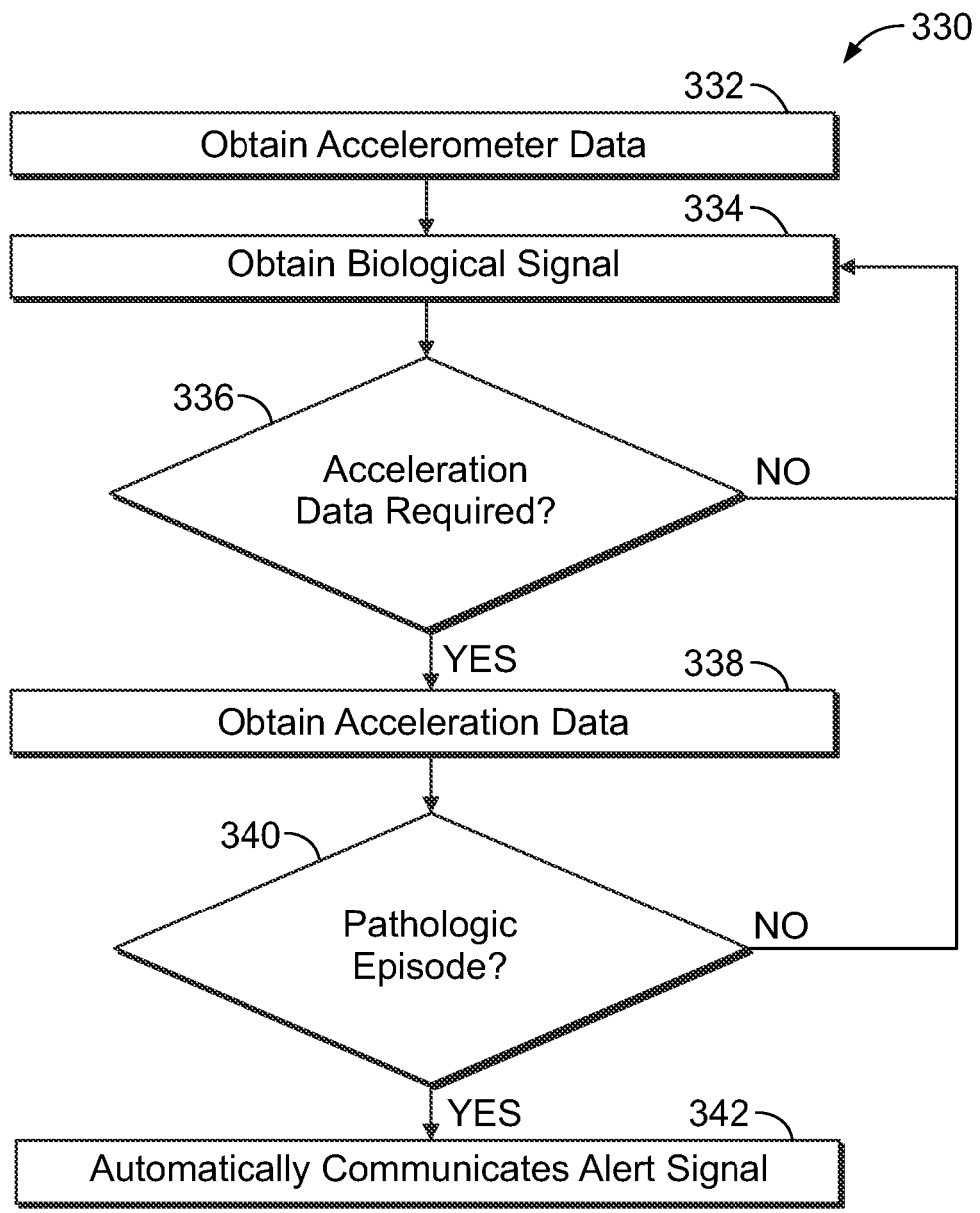
FIG. 3C illustrates a flow block diagram of a method for diagnosing a pathologic episode in accordance with embodiments herein.

FIG. 3C illustrates a method 330 for diagnosing a pathologic episode of a patient. In one example the monitoring system used to perform the method includes an accelerometer, similar to that illustrated in FIG. 1. By monitoring the physical actions of a patient using an accelerometer, potentially adverse pathologic episodes, or conditions may be diagnosed.

Non-limiting examples of pathologic episodes include heart failure, stroke, syncope, arrythmia, heart attack, asystole, brady event, neurological episodes, ventricular fibrillation (VF), ventricular tachycardia (VT), a diabetic seizure, and epileptic seizure, or any other type of seizure, episodes that may result from substantial reduction or change in pulmonary arterial pressure and the like. Specifically, to reduce a false detection of a pathologic episode, such as a syncope, accelerometer data may be utilized in making a diagnosis of the pathologic episode. In particular, once a biological signal is obtained that meeting a determined condition, the acceleration data obtained after the biological signal is compared to the acceleration data obtained before the biological signal to determine a diagnosis of a pathologic episode.

At 332, one or more processors obtain accelerometer data before obtaining a biological signal. In particular, an accelerometer obtains the accelerometer data along at least one axis. The accelerometer data may include IMD accelerometer data, activity related data, posture related data, or the like. The IMD accelerometer data may be obtained from any of the three axes in any manner described herein. The posture related data of the accelerometer may similarly be obtained from any axis or may be a composite of the axes. The accelerometer in one example may be programed to obtain the accelerometer data continuously, during constant intervals. In one embodiment, the accelerometer obtains the accelerometer data once every minute. In another example, the accelerometer obtains the accelerometer data once every four minutes. Alternatively the interval can be greater than four minutes, less than one minute, etc. In this manner the accelerometer obtains the accelerometer data at a first rate where the first rate is representative the how often, or the interval between times the accelerometer obtains the accelerometer data before a biological signal is received.

At 334, a monitoring device operates to obtain a biological signal. In one embodiment, the monitoring device is an IMD. In one embodiment, the IMD is an ICM that monitors cardiac activity signals of the heart for arrythmias (e.g., heart attacks, VFs, VTs, syncope, etc.). Additionally or alternatively, the IMD may be a BGA device, such as described in the '870 Provisional Application. The biological signal may be any signal that provides information about pathologic condition of a patient, including acceleration signals, cardiac activity signals, heart sound signals, impedance signals, pulmonary arterial pressure signals, signals indicative of a diabetic seizure, signals indicative of an epileptic seizure, or signals indicative of any other type of seizure and the like. Specifically, the biological signal may be used by a monitoring device, such as an ICM, a BGA device, PAP sensor or otherwise to detect a pathologic episode.

At 336, one or more processors determine if acceleration data is required to make a diagnosis based on the biological signal obtained. Specifically, the determination may be made by utilizing determined conditions such as ranges, thresholds, or the like that are representative of a potential pathologic episode. In this method, the acceleration data is utilized to diagnose a pathologic episode instead of verifying a pathologic episode has occurred. In this manner, the ranges, thresholds, etc. can have greater variance because additional information in the form of accelerometer data is to be utilized to make the diagnosis. By having a greater variance, less chance of missing or misdiagnosing a pathologic episode is achieved. The determination may include applying an application specific model to calculate whether additional information is required. Similarly, a lookup table, decision tree, mathematical function, or the like can be utilized to determine if the determined conditions are presented.

If at 336, acceleration data is not required to make a diagnosis, the one or more processors continue to monitor and obtain additional biological signals at 334. However, if at 336, a determination is made that acceleration data is required for diagnosis, then at 338, the one or more processors obtains acceleration data for a period after obtaining the biological signal. In one example, the period is a preset time of one minute, two minutes, three minutes, five minutes, or the like. In one embodiment the acceleration data continues to be obtained at the first rate and the period allows enough time for the acceleration to be obtained based on the first rate. In another embodiment, (as provided in FIG. 3D) the determination that acceleration data is required to make a diagnosis automatically triggers the accelerometer to obtain acceleration data, and causes the acceleration data to be obtained at a second faster rate. So, if the first rate resulted in the accelerometer receiving acceleration data every four minutes, the second rate can cause accelerometer data to be received every thirty seconds. In this manner, more information is received by the accelerometer that may be utilized for diagnosis of a pathologic episode.

At 340, the biological signal and obtained accelerometer data are analyzed to determine if a diagnosis of a pathologic episode can be made. In one embodiment, the biological signal and a physical action of an individual detected by the accelerometer data are utilized to diagnose the pathologic episode. To make the diagnosis, the accelerometer data obtained from after obtaining the biological signal for a period can be compared to the accelerometer data obtained before the biological signal for a period. Specifically, the period may be the same or different.

In one example, because at a first rate accelerometer data is only obtained once every four minutes, the period before the biological signal is obtained is twelve minutes, while because at the second rate accelerometer data is obtained every 30 second, the period after the biological signal is obtained is four minutes. In one example, the acceleration data shows an individual is standing for the twelve minutes before the biological signal is obtained, whereas after the biological signal is obtained the individual is constantly laying on the floor for four straight minutes. In other example, the periods are of equal length. In yet other embodiment, a comparison is not made, but instead the cumulative acceleration data can be utilized to make a diagnosis. For example, when a patient begins having a seizure in their sleep, the acceleration data obtained in the four minutes before obtaining the biological signal indicates that the patient is laying down, while the four minutes after obtaining the biological signal the acceleration data indicates the individual is shaking or convulsing.

If at 340 a pathologic episode is not diagnosed, the monitoring device continues to obtain biological signals at 334. However, if a pathologic episode is diagnosed that 340, then at 342 the monitoring device automatically communicates an alert signal in response to the diagnosis of the pathologic episode, and/or provides treatment for the pathologic episode. The alert signal may be communicated to a remote device, emergency services, hospital, doctor's office and/or phone, clinician office and/or phone, third party, PDE, home monitoring device, etc. The alert signal may include an auditory alarm or sound, flashing lights, or the like to bring attention to the alert signal. The monitoring device may also record the pathologic episode, accelerometer data, activity related data, posture related data, or the like resulting in the transmission of the alert signal. Additionally, in one example, when the monitoring device also represents an IMD configured to deliver therapy, a treatment may be provided including pacing, shock, release of medication (e.g. insulin), etc. In this manner, the treatment may immediately be provided for the patient.

Figure 3D:
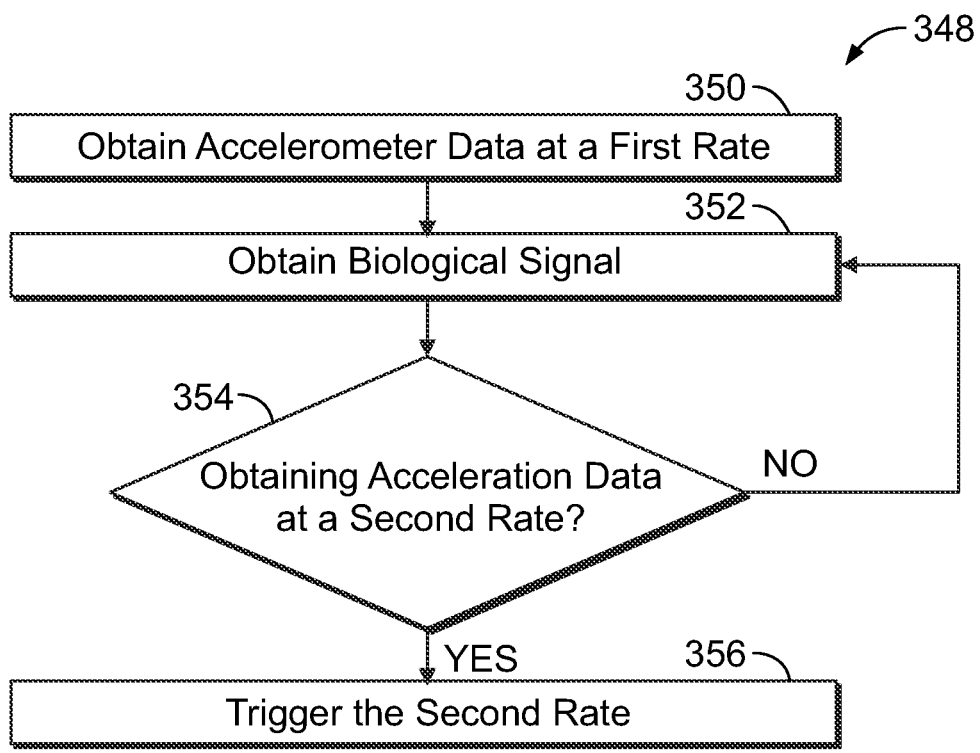
FIG. 3D illustrates a flow block diagram of a method for triggering obtaining accelerometer data in accordance with embodiments herein.

FIG. 3D illustrates a method 348 for triggering obtaining accelerometer data in accordance with embodiments herein. In one example the monitoring system used to perform the method includes an accelerometer, similar to that illustrated in FIG. 1.

At 350, the monitoring device obtains accelerometer data at a first rate before obtaining a biological signal. In particular, an accelerometer obtains the accelerometer data along at least one axis. The accelerometer data may include IMD accelerometer data, activity related data, posture related data, or the like. The IMD accelerometer data may be obtained from any of the three axes in any manner described herein. The posture related data of the accelerometer may similarly be obtained from any axis or may be a composite of the axes. The accelerometer in one example may be programed to obtain the accelerometer data continuously at the first rate. In one embodiment, the accelerometer obtains the accelerometer data once every minute. In another example, the accelerometer obtains the accelerometer data once every four minutes. Alternatively the interval can be greater than four minutes, less than one minute, etc. In this manner the accelerometer obtains the accelerometer data at a first rate where the first rate is representative the how often, or the interval between times the accelerometer obtains the accelerometer data before a biological signal is received.

At 352, a monitoring device operates to obtain a biological signal. In one embodiment, the monitoring device is an IMD. In one embodiment, the IMD is an ICM that monitors cardiac activity signals of the heart for arrythmias (e.g., heart attacks, VFs, VTs, syncope, etc.). Additionally or alternatively, the IMD may be a BGA device, such as described in the '870 Provisional Application. The biological signal may be any signal that provides information about pathologic condition of a patient, including acceleration signals, cardiac activity signals, heart sound signals, impedance signals, pulmonary arterial pressure signals, signals indicative of a diabetic seizure, signals indicative of an epileptic seizure, or signals indicative of any other type of seizure and the like. Specifically, the biological signal may be used by a monitoring device, such as an ICM, a BGA device, PAP sensor or otherwise to detect a pathologic episode.

At 354, the monitoring device determines if obtaining acceleration data at a second rate is to be triggered. In one example, the biological signal is utilized to provide a candidate pathologic episode that is then is to be verified as a pathologic episode by accelerometer data as described in the embodiment of FIG. 3A. In another embodiment, the biological signal and accelerometer data are utilized to diagnose the pathologic episode as described in the embodiment of FIG. 3C. In each instance, accelerometer data is required to be obtained at a faster rate after the biological signal has been obtained. By obtaining the accelerometer data at a faster, second rate, analysis of the accelerometer data is improved for verification or diagnosis of a pathologic episode.

If at 354 obtaining acceleration data at a second rate is not triggered, the monitoring device continues to obtain the acceleration data and biological signal. If at 354, obtaining acceleration data at a second rate is triggered, then at 356 the monitoring device triggers the second rate. In one example, the monitoring device automatically obtains acceleration data upon the determination to trigger obtaining the acceleration data at the second rate. For example, if the monitoring device is obtaining acceleration data at a first rate of every four minutes, and the determination is made to trigger obtaining the acceleration data at the second rate one minute after the last acceleration data was obtained at the first rate, the monitoring device immediately obtains the acceleration data. The monitoring device also begins obtaining data at the second rate. In one embodiment, the acceleration data is obtained every thirty seconds after the monitoring device has triggered obtaining the acceleration data at the second rate. In other embodiments, the second rate can be more or less that thirty seconds. Still, the second rate is faster than the first rate to provide additional acceleration data to review of diagnosis and treatment.

Figure 4A:
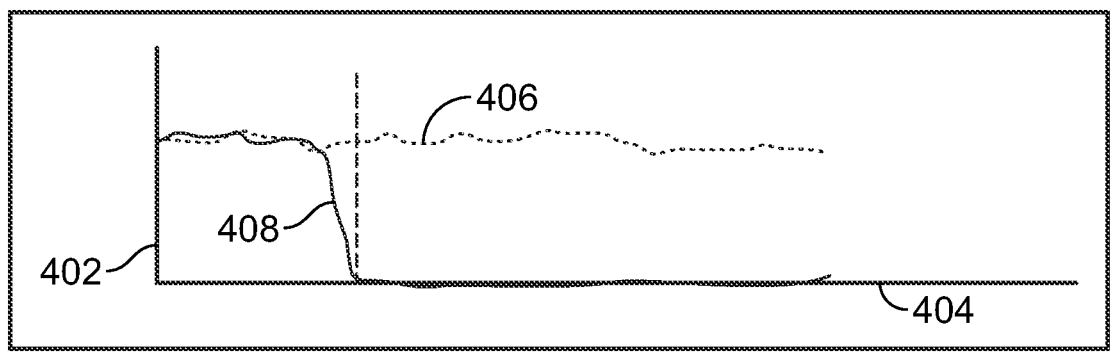
FIG. 4A illustrates a graph of activity of a patient over time in accordance with embodiments herein.

FIG. 4A illustrates accelerometer data that may be analyzed to verify a candidate pathologic episode as described in relation to 308. Specifically, the combination of accelerometer data from all three axes can be used to quantify subject posture with respect to gravity, and activity. By quantifying activity and posture using all three axes, the accelerometer signals may be used for numerous purposes. In the embodiment, the accelerometer data provides an activity level of a patient 402 over time 404 for an interval based on the accelerometer signals. In one example, the amplitude of a combined accelerometer signal correlates with an activity level. In this manner, line 406 represents the activity level of a patient measured by an accelerometer over time that is not experiencing a pathologic episode. In contrast, line 408 represents the activity level of a patient measured by an accelerometer over time that is experiencing a syncopal event. As shown, the accelerometer reading may be used to verify the existence of a pathologic episode.

In an alternative embodiment, the accelerometer continuously monitors the patient. Based on the continuous monitoring, when an activity level of the patient is detected as going to, or approaching zero, as illustrated in FIG. 4A, an alert signal may be communicated to a remote device. In particular, even without the detection of a pathologic episode, the accelerometer may detect an actual episode that is not detected by the monitoring device, or a patient that has fallen. By communicating an alert signal to a remote device, the patient may be checked on by a third party to ensure a pathologic episode, or a fall that the patient cannot get up from, has occurred.

Figure 4B:
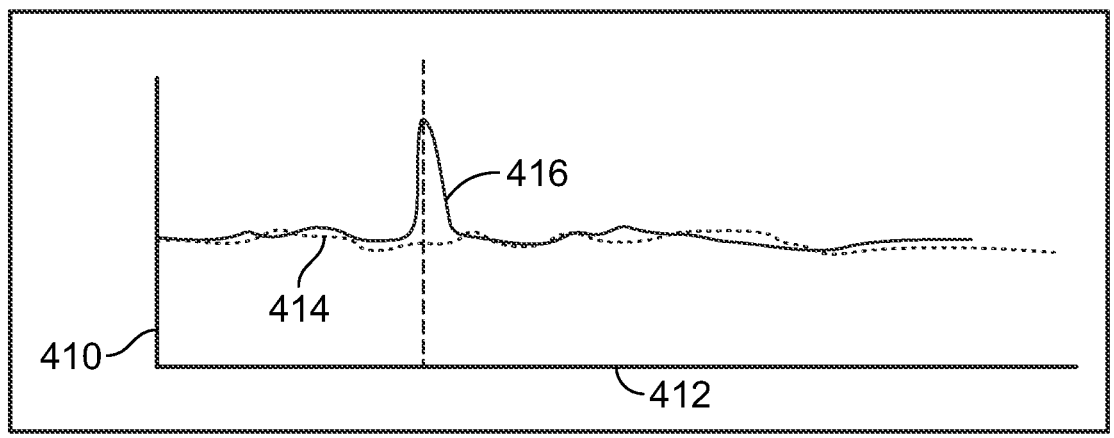
FIG. 4B illustrates a graph of patient position over time in accordance with embodiments herein.

FIG. 4B illustrates alternative accelerometer data that may be analyzed to verify a candidate pathologic episode as described in relation to 308. In the embodiment, accelerometer data is provided that includes a change in position of each axis 410 of the accelerometer over time 412, and the sum of the changes is obtained. The change in position may be determined by comparing the position of the accelerometer based on an accelerometer signal at a first time, and the position of the accelerometer based on an accelerometer signal at a second time. Line 414 represents the change of position of each axis over time of a patient that is not experience a pathologic episode, while line 416 represents the change of position of each axis over time of a patient that is experiencing a pathologic episode.

Figure 5:
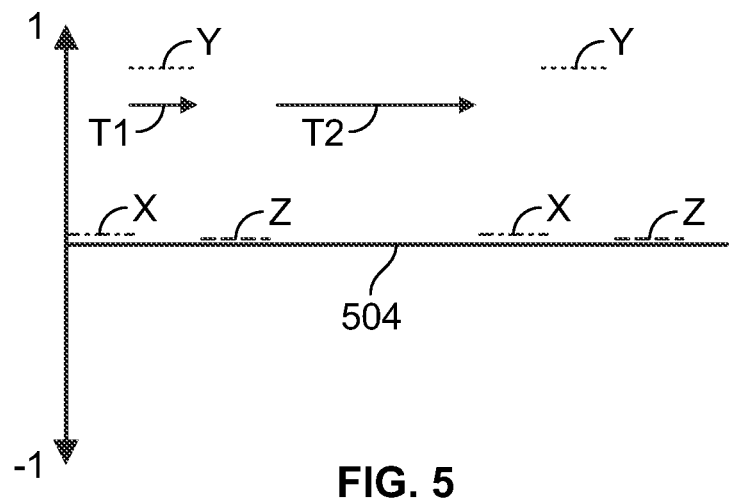
FIG. 5 illustrates a graph for measuring activity of a patient in accordance with embodiments herein.

FIG. 5 is directed toward using the accelerometer in a manner to saves battery usage while continuing to obtain accelerometer data that may be used as described in relation to the method of FIG. 3. FIG. 5 illustrates a graphical example of a timing pattern that may be utilized in connection with managing measurement of accelerometer signals in accordance with embodiments herein. The horizontal axis 504 represents time, while the markers X, Y and Z denote intervals of time during which accelerometer signals from the accelerometer are collected for the corresponding axis. For example, accelerometer signals are initially collected from the accelerometer output/channel the corresponds to the X axis of the accelerometer (also referred to as the X axis output or X axis channel). Thereafter, the device stops collecting accelerometer signals from the X axis output/channel and switches to the output or channel corresponding to the y-axis of the accelerometer. During the time interval T1 accelerometer signals are collected from the output/channel corresponding to the y-axis (also referred to as the y-axis output or y-axis channel). At expiration of the time interval T1, the device stops collecting accelerometer signals from the y-axis output/channel and switches to the output or channel corresponding to the Z axis of the accelerometer. During a corresponding time interval, accelerometer signals are collected from the output/channel corresponding to the Z axes (also referred to as the Z axis output or Z axis channel). At the expiration of the time interval for collecting Z axes accelerometer signals, the device stops collecting accelerometer signals from the Z axis output/channel.

The X axis is sampled for a first portion of a first data collection interval, while a second axis is sampled for a second portion of the first data collection interval that does not overlap with the first portion, and a third axis is sampled for a third portion of the first data collection interval that does not overlap with the first portion or second portion of the first data collection interval. A second data collection interval T2 may then be used to control the duty cycle of reading measurements.

In one embodiment, a same or common time interval may be utilized while collecting X, Y and Z axes accelerometer signals. Additionally or alternatively, different time intervals may be utilized in connection with each of the X, Y and Z channels. For example, Y axis accelerometer signals may be collected during a first time interval T1, whereas a different second time interval T2 may be utilized for collecting X axis accelerometer signals and/or y-axis accelerometer signals. It is recognized that the order in which accelerometer signals are collected from the various channels may vary. Also, one channel may be sampled more often than the other channels. For example, the X axis channel may be sampled twice as often as the Z axis channel, such as when the activity of interest or purpose for collecting the accelerometer signals indicates that one axis may have more relevant information.

The X, Y and Z axis accelerometer signals are stored as an X axis accelerometer data set, a y-axis accelerometer data set and Z axes accelerometer data set. Thereafter, the accelerometer may enter an idle state for a desired time interval, such as the time interval T2. When the time interval T2 expires, the accelerometer may repeat the collection of accelerometer signals along the various channels. The time intervals may be managed in various manners. For example, a hardware timing circuit may be utilized to define the various time intervals T1 and T2. Additionally or alternatively, firmware may be utilized to set and countdown corresponding time intervals T1 and T2.

In accordance with new and unique aspects herein, it has been found that accelerometer signals need not be simultaneously collected along all three channels. By managing the manner in which accelerometer signals are obtained in a serial manner, embodiments herein reduce the energy consumption utilized when monitoring posture.

In yet another embodiment, energy may be conserved by managing the measurement duty cycle and/or by switching circuitry between awake and asleep states based on various criteria. For example, a processor or control circuitry for the accelerometer may reduce energy consumption by powering off some or all circuitry associated with collecting and processing accelerometer signals between data collection intervals, also referred to as a posture acquisition duty cycle. The posture acquisition duty cycle may be increased by increasing the amount of time between accelerometer signal measurements. Alternatively or alternatively, the processor and/or control circuitry may power down (or set to an in active state) 2 two out of 3 accelerometer output channels, such that accelerometer signals are only collected from a single channel periodically. The accelerometer signals from the single active channel may be sampled periodically and analyzed. The analysis may include determining whether the accelerometer signals from the active channel satisfy one or more criteria. For example, the condition may be whether the accelerometer signals for the single active channel exhibit a level of activity of the patient that is greater than a determined threshold. When the activity of the patient over the single active channel exceeds the threshold, the processor or control circuitry may wake up, activate, or simply begin to collect accelerometer signals from one or both of the other two channels. Thereafter, two or more of the three channels may then be sampled simultaneously or serially (e.g. as described in relation to FIG. 4) for a predetermined number to next duty cycles or for a period of time defined by other criteria (e.g. until an activity of the patient of interest has stopped. To this end, channels may be powered off during segments of low activity of the patient to further reduce energy consumption. For example, the device may be configured to operate at reduced energy and/or while monitoring only a single channel during an activity acquisition sleep time. During a determined period, when no measurement is desired, or when activity of the patient is unlikely, the processor and/or acquisition control circuitry may turn off for a determined interval of time. Alternatively, acquisition of accelerometer signals over 2 out of the 3 axes may be suspended and a single axis may only be sampled periodically (e.g. every ten minutes during a two hour interval) and when change is detected in the single axis measurement greater than a specific threshold, all activity channels are then sampled. Alternatively, activity channels may be suspended into low-power mode during segments of stable posture and switched to full power when a change of posture is detected.

The foregoing examples described somewhat independent analysis of the accelerometer signals captured over the various channels. Additionally or alternatively, acceleration signals from two or more of the channels may be combined in certain instances to collect certain types of information. For example, a composite activity signal may be derived by calculating an average value of the accelerometer signals over the X-axis, Y-axis, and Z-axis channels for a predetermined period of time (e.g. one second), where the three accelerometer signals are measured simultaneously. The composite activity signal is independent of the orientation of the accelerometer. For example, the accelerometer may be positioned such that the Y-axis of the accelerometer predominantly measures the activity-related acceleration of the patient, whereas the X axis and Z axis accelerometer signals may provide very little information indicative of activity of the patient. Nonetheless, when all three signals are combined, the resulting composite activity signal affords a good indicator of overall activity of the patient regardless of the accelerometer orientation. In accordance with embodiments herein, methods and systems may utilize the composite activity signal to monitor activity intensity or activity tolerance, including the identification of positive or negative trends therein.

Optionally, methods and systems herein may identify one or a subset of the accelerometer channels that may be better suited to provide long term monitoring. For example, during implantation, or the days following implantation, a processor of an IMD or control circuitry of the accelerometer may cycle through the accelerometer signals from the X, Y, and Z axes channels. The accelerometer signals from the various channels are analyzed to identify the channel that exhibits a characteristic of interest, such as the largest amount of activity of the patient, the most frequent changes in activity of the patient, a signal level that is the more accurate indicator of particular types of activity of the patient, and the like. The identify channel may then be designated as the primary or base channel that is utilized for long-term monitoring, while the other channels are set to an in active state or a sleep mode.

Figure 6:
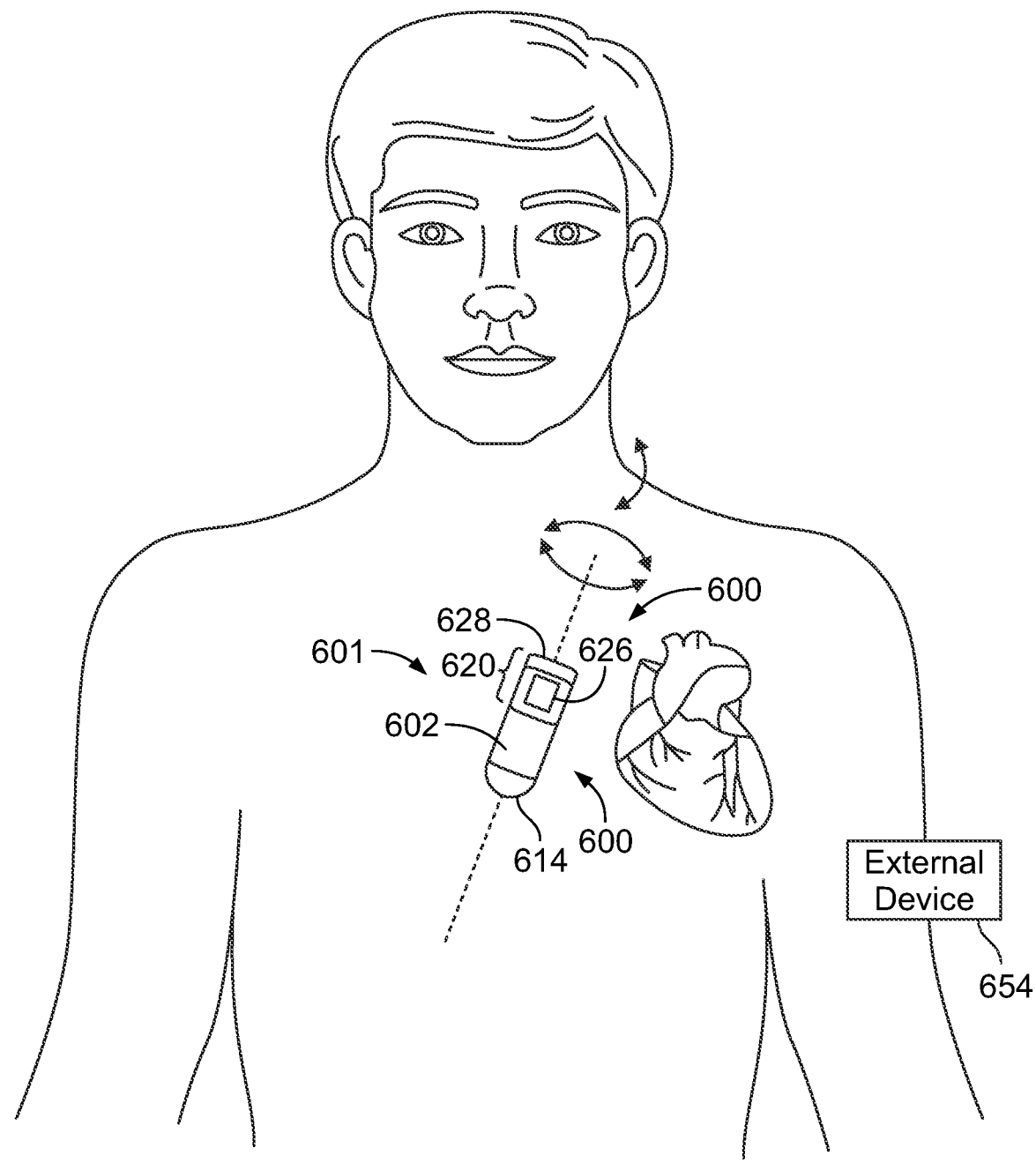
FIG. 6 illustrates an implantable cardiac monitoring device (ICM) intended for subcutaneous implantation at a site near the heart in accordance with embodiments herein.

FIG. 6 illustrates an example monitoring device 600 that is an IMD intended for subcutaneous implantation at a site near the heart that may house a monitoring system 601. In one example the monitoring system 601 is the monitoring system described in FIG. 1. The monitoring device 600 is illustrated as exemplary only, and the monitoring system 601 may be included in other systems. The monitoring device 600 includes two or more spaced-apart sense electrodes 614, 626 positioned with respect to a housing 602. The sense electrodes 614, 626 provide for detection of far field electrogram signals. The header 620 includes an antenna 628 and the electrode 626. The antenna 628 is configured to wirelessly communicate with an external device 654 in accordance with one or more predetermined wireless protocols (e.g., Bluetooth, Bluetooth low energy, Wi-Fi, etc.).

The housing 602 includes various other components such as: sense electronics for receiving signals from the electrodes, a microprocessor for analyzing the far field CA signals, including assessing the presence of R-waves in cardiac beats occurring while the monitoring device is in different locations relative to gravitational force, a loop memory for temporary storage of CA data, a device memory for long-term storage of CA data, sensors for detecting activity of the patient, including an accelerometer for detecting acceleration signatures indicative of heart sound, and a battery for powering components.

The monitoring device 600 may sense far field, subcutaneous CA signals, processes the CA signals to detect arrhythmias and if an arrhythmia is detected, automatically records the CA signals in memory for subsequent transmission to an external device 654.

The monitoring device 600 is implanted in a position and orientation such that, when the patient stands, the monitoring device 600 is located at a reference position and orientation with respect to a global coordinate system that is defined relative to a gravitational direction. For example, the gravitational direction may be along the Z-axis while the X-axis is between the left and right arms.

Figure 7:
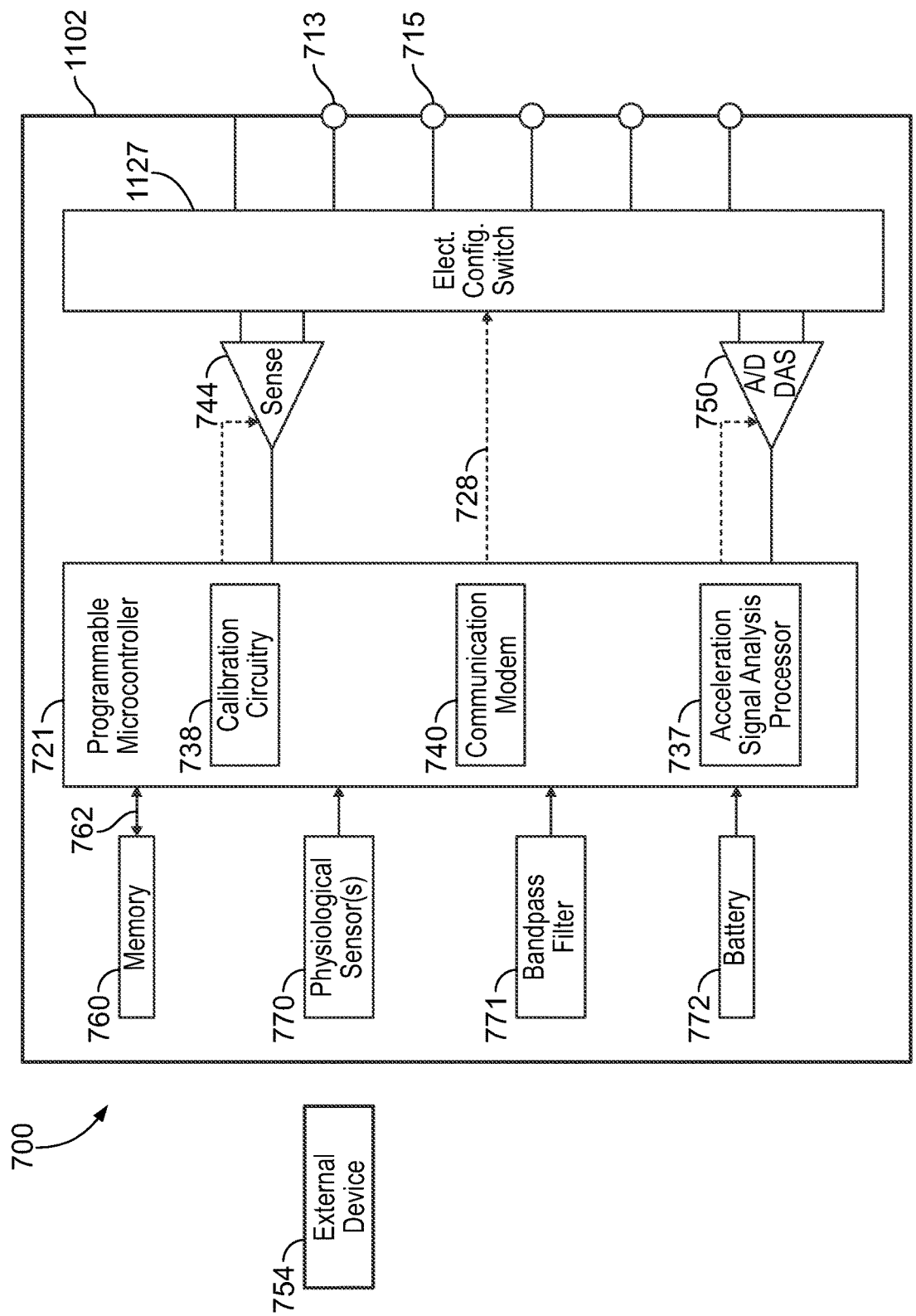
FIG. 7 illustrates a block diagram of the ICM formed in accordance with embodiments herein.

FIG. 7 shows a block diagram of the monitoring device 600 formed in accordance with embodiments herein. The monitoring device 600 has a housing 602 to hold the electronic/computing components. The housing 602 (which is often referred to as the "can," "case," "encasing," or "case electrode") may be programmably selected to act as an electrode for certain sensing modes. Housing 602 further includes a connector (not shown) with at least one terminal 713 and optionally additional terminals 715. The terminals 713, 715 may be coupled to sensing electrodes that are provided upon or immediately adjacent the housing 602. Optionally, more than two terminals 713, 715 may be provided in order to support more than two sensing electrodes, such as for a bipolar sensing scheme that uses the housing 602 as a reference electrode. Additionally or alternatively, the terminals 713, 715 may be connected to one or more leads having one or more electrodes provided thereon, where the electrodes are located in various locations about the heart. The type and location of each electrode may vary.

A switch 727 is optionally provided to allow selection of different electrode configurations under the control of the microcontroller 721. The electrode configuration switch 727 may include multiple switches for connecting the desired electrodes to the appropriate I/O circuits, thereby facilitating electrode programmability. The switch 727 is controlled by a control signal 728 from the microcontroller 721. Optionally, the switch 727 may be omitted and the I/O circuits directly connected via terminals 713, 715.

The monitoring device 600 includes sensing circuit 744 selectively coupled to one or more electrodes that perform sensing operations, through the switch 727 to detect cardiac activity data indicative of cardiac activity. Optionally, the sensing circuit 744 may be removed entirely, and the microcontroller 721 perform the operations described herein based upon the CA signals from the ND data acquisition system 750 directly coupled to the electrodes. The output of the sensing circuit 744 is connected to the microcontroller 721 which, in turn, determines when to store the cardiac activity data of CA signals (digitized by the ND data acquisition system 750) in the memory 760.

The monitoring device 600 includes a programmable microcontroller 721 that controls various operations of the monitoring device 600, including cardiac monitoring. Microcontroller 721 includes a microprocessor (or equivalent control circuitry), RAM and/or ROM memory, logic and timing circuitry, state machine circuitry, and I/O circuitry. The microcontroller 721 is configured to implement the operations described herein in connection with collecting and analyzing accelerometer signals.

The microcontroller 721 may also include calibration circuitry 738 that is configured to implement the calibration operations described herein. Among other things, the calibration circuitry 738 obtains baseline accelerometer signals from an accelerometer 770 in connection with specific patient postures. The postures may include supine, standing, laying on a right side, laying on are left side, angled, or the like. The calibration circuitry 738 may also calculate synthetic baseline accelerometer signals based on orthogonal baseline accelerometer signals that are directly measured by the accelerometer 770 as described herein. Although not shown, the microcontroller 721 may further include other dedicated circuitry and/or firmware/software components that assist in monitoring various conditions of the patient's heart and managing pacing therapies.

The monitoring device 600 is further equipped with a communication modem (modulator/demodulator) 740 to enable wireless communication. In one implementation, the communication modem 740 uses high frequency modulation, for example using RF, Bluetooth, or Bluetooth Low Energy telemetry protocols. The signals are transmitted in a high frequency range and will travel through the body tissue in fluids without stimulating the heart or being felt by the patient. The communication modem 740 may be implemented in hardware as part of the microcontroller 721, or as software/firmware instructions programmed into and executed by the microcontroller 721. Alternatively, the modem 740 may reside separately from the microcontroller as a standalone component, or external device 754. The modem 740 facilitates data retrieval from a remote monitoring network. The modem 740 enables timely and accurate data transfer directly from the patient to an electronic device utilized by a physician.

By way of example, the external device 754 may represent a bedside monitor installed in a patient's home and utilized to communicate with the monitoring device 600 while the patient is at home, in bed or asleep. The external device 754 may be a programmer used in the clinic to interrogate the monitoring device 600, retrieve data and program detection criteria and other features. The external device 754 may be a PDE (e.g., smartphone, tablet device, laptop computer, smartwatch, and the like) that can be coupled over a network (e.g., the Internet) to a remote monitoring service, medical network and the like. The external device 754 facilitates access by physicians to patient data as well as permitting the physician to review real-time accelerometer data sets as collected by the monitoring device 600.

The microcontroller 721 is coupled to a memory 760 by a suitable data/address bus 762. The memory 760 stores the accelerometer signals, accelerometer data sets, reference posture related data sets, cardiac activity signals, as well as the markers and other data content associated with detection and determination of the condition of the heart of the patient.

The monitoring device 600 can further include one or more accelerometer circuits 770. For example, the accelerometer circuits 770 may be part of a monitoring system 701, or may represent one or more accelerometers, such as a three-dimensional (3D) accelerometer. The accelerometer circuits 770 may utilize a piezoelectric, a piezoresistive, and/or capacitive components are commonly used to convert the mechanical motion of the 3D accelerometer into an electrical signal received by the microcontroller 721. By way of example, the 3-D accelerometer may three outputs/channels that generate three corresponding electrical signals indicative of motion in three corresponding directions, namely X, Y and Z directions. The electrical signals associated with each of the three directional components may be divided into different frequency components to obtain different types of information therefrom.

The accelerometer circuits 770 collect device location information with respect to gravitational force while the monitoring device 600 collects cardiac activity signals in connection with multiple cardiac beats. In one example, the accelerometer circuits 770 include the accelerometer as described in relation to FIG. 1. The microcontroller 721 may utilize the signals from the accelerometer circuits 770. While shown as being included within the housing 602, the accelerometer circuit 770 may be external to the housing 602, yet still, be implanted within or carried by the patient.

A battery 772 provide operating power to all of the components in the monitoring device 600. The battery 772 is capable of operating at low current drains for long periods of time. The battery 772 also desirably has a predictable discharge characteristic so that elective replacement time can be detected.

Figure 8:
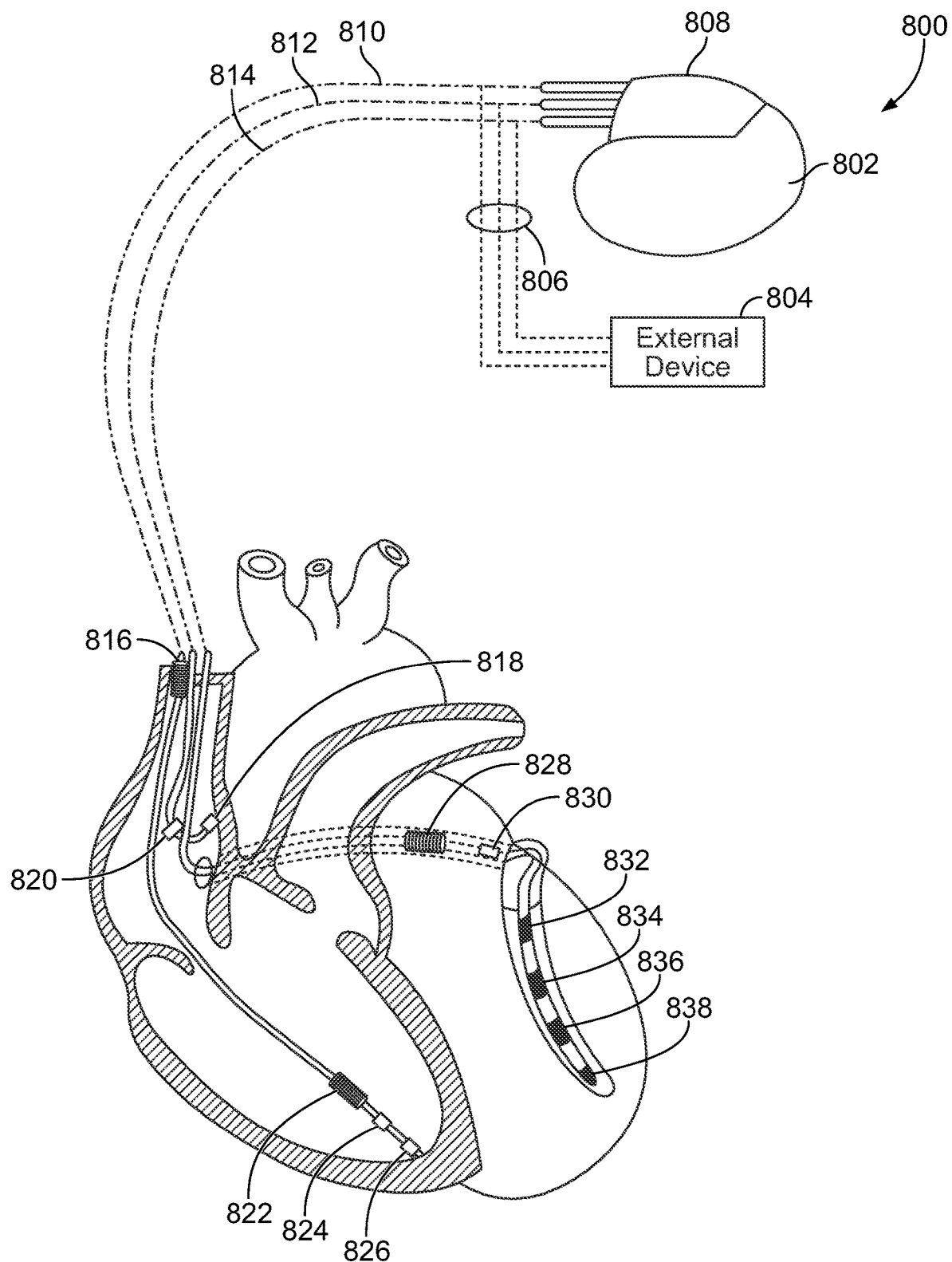
FIG. 8 illustrates an implantable medical device (IMD) intended for subcutaneous implantation at a site near the heart in accordance with embodiments herein.

FIG. 8 illustrates an alternative monitoring device 800 that may apply treatment, such as a shock when a candidate pathologic episode such as VF or VT is verified using the method of FIG. 3. The monitoring device 800 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. The monitoring device 800 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. Exemplary structures for the monitoring device 800 are discussed and illustrated in the drawings herewith.

The monitoring device 800 includes a housing 802 that is joined to a header assembly 809 that holds receptacle connectors connected to a right ventricular lead 810, a right atrial lead 812, and a coronary sinus lead 814, respectively. The leads 812, 814 and 810 measure cardiac signals of the heart. The right atrial lead 812 includes an atrial tip electrode 818 and an atrial ring electrode 820. The coronary sinus lead 814 includes a left atrial ring electrode 828, a left atrial coil electrode 830 and one or more left ventricular electrodes 832-838 (e.g., also referred to as P1, M1, M2 and D1) to form a multi-pole LV electrode combination. The right ventricular lead 810 includes an RV tip electrode 826, an RV ring electrode 824, an RV coil electrode 822, and an SVC coil electrode 816. The leads 812, 814 and 810 detect IEGM signals that are processed and analyzed as described herein. The leads 812, 814 and 810 also delivery therapies as described herein.

During implantation, an external device 804 is connected to one or more of the leads 812, 814 and 810 through temporary inputs 803. The inputs 803 of the external device 804 receive IEGM signals from the leads 812, 814 and 810 during implantation and display the IEGM signals to the physician on a display. Hence, the external device 804 receives the IEGM cardiac signals through telemetry circuit inputs. The physician or another user controls operation of the external device 804 through a user interface.

Figure 9:
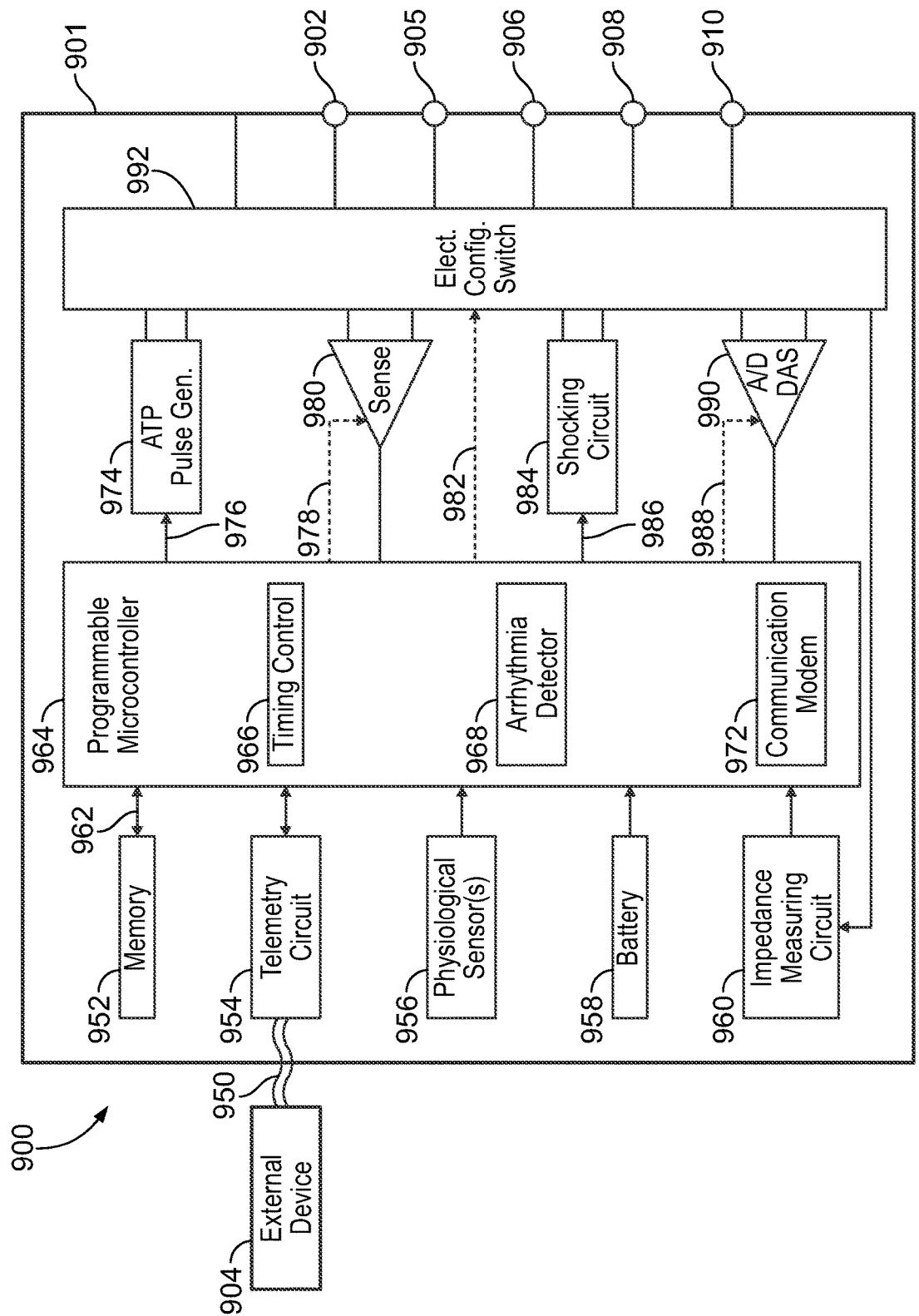
FIG. 9 illustrates a block diagram of the IMD formed in accordance with embodiments herein.

FIG. 9 illustrates an example block diagram of a monitoring device 900 that is implanted into the patient as part of the implantable cardiac system. In one example, the monitoring device 900 is an IMD. The monitoring device 900 may be implemented as a full-function biventricular pacemaker, equipped with both atrial and ventricular sensing and pacing circuitry for four chamber sensing and stimulation therapy (including both pacing and shock treatment). Optionally, the monitoring device 900 may provide full-function cardiac resynchronization therapy. Alternatively, the monitoring device 900 may be implemented with a reduced set of functions and components. For instance, the monitoring device may be implemented without ventricular sensing and pacing.

The monitoring device 900 has a housing 901 to hold the electronic/computing components. The housing 901 (which is often referred to as the "can", "case", "encasing", or "case electrode") may be programmably selected to act as the return electrode for certain stimulus modes. Housing 901 further includes a connector (not shown) with a plurality of terminals 902, 905, 906, 908, and 911. The type and location of each electrode may vary. For example, the electrodes may include various combinations of ring, tip, coil and shocking electrodes and the like.

The monitoring device 900 includes a programmable microcontroller 964 that controls various operations of the monitoring device 900. Microcontroller 964 includes a microprocessor (or equivalent control circuitry), RAM and/or ROM memory, logic and timing circuitry, state machine circuitry, and I/O circuitry. The monitoring device 900 further includes a first chamber pulse generator 974 that generates stimulation pulses for delivery by one or more electrodes coupled thereto. The pulse generator 974 is controlled by the microcontroller 964 via control signal 976. The pulse generator 974 is coupled to the select electrode(s) via an electrode configuration switch 992, which includes multiple switches for connecting the desired electrodes to the appropriate I/O circuits, thereby facilitating electrode programmability. The switch 992 is controlled by a control signal 986 from the microcontroller 964.

Microcontroller 964 is illustrated to include timing control circuitry 966 to control the timing of the stimulation pulses (e.g., pacing rate, atrio-ventricular (AV) delay, atrial interconduction (A-A) delay, or ventricular interconduction (V-V) delay, etc.). Microcontroller 964 also has an arrhythmia detector 968 for detecting arrhythmia conditions. Although not shown, the microcontroller 964 may further include other dedicated circuitry and/or firmware/software components that assist in monitoring various conditions of the patient's heart and managing pacing therapies.

The monitoring device 900 is further equipped with a communication modem (modulator/demodulator) 972 to enable wireless communication with other devices, implanted devices, and/or external devices. The monitoring device 900 includes sensing circuitry 980 selectively coupled to one or more electrodes that perform sensing operations, through the switch 992, to detect the presence of cardiac activity.

The output of the sensing circuitry 980 is connected to the microcontroller 964 which, in turn, triggers or inhibits the pulse generator 974 in response to the absence or presence of cardiac activity. The sensing circuitry 980 receives a control signal 978 from the microcontroller 964 for purposes of controlling the gain, threshold, polarization charge removal circuitry (not shown), and the timing of any blocking circuitry (not shown) coupled to the inputs of the sensing circuitry.

In the example of FIG. 9, a single sensing circuit 980 is illustrated. Optionally, the monitoring device 900 may include multiple sensing circuit, similar to sensing circuit 980, where each sensing circuit is coupled to one or more electrodes and controlled by the microcontroller 964 to sense electrical activity detected at the corresponding one or more electrodes. The sensing circuit 980 may operate in a unipolar sensing configuration or in a bipolar sensing configuration.

The monitoring device 900 further includes an analog-to-digital (ND) data acquisition system (DAS) 990 coupled to one or more electrodes via the switch 992 to sample cardiac signals across any pair of desired electrodes. The microcontroller 964 is also coupled to a memory 952 by a suitable data/address bus 962. The programmable operating parameters used by the microcontroller 964 are stored in memory 952 and used to customize the operation of the monitoring device 900 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The telemetry circuit 954 allows intracardiac electrograms and status information relating to the operation of the monitoring device 900 (as contained in the microcontroller 964 or memory 952) to be sent to the external device 904 through the established communication link 950.

The monitoring device 900 can further include one or more physiologic sensors 956. Such sensors are commonly referred to as "rate-responsive" sensors because they are typically used to adjust pacing stimulation rates according to the exercise state of the patient. However, the physiological sensor 956 may further be used to detect changes in cardiac output, changes in the physiological condition of the heart, or diurnal changes in activity (e.g., detecting sleep and wake states).

A battery 958 provides operating power to all of the components in the monitoring device 900. The monitoring device 900 further includes an impedance measuring circuit 960, which can be used for many things, including: lead impedance surveillance during the acute and chronic phases for proper lead positioning or dislodgement; detecting operable electrodes and automatically switching to an operable pair if dislodgement occurs; measuring thoracic impedance for determining shock thresholds; detecting when the device has been implanted; measuring stroke volume; and detecting the opening of heart valves; and so forth. The impedance measuring circuit 960 is coupled to the switch 992 so that any desired electrode may be used. The monitoring device 900 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 964 further controls a shocking circuit 984 by way of a control signal 986.

Figure 10:
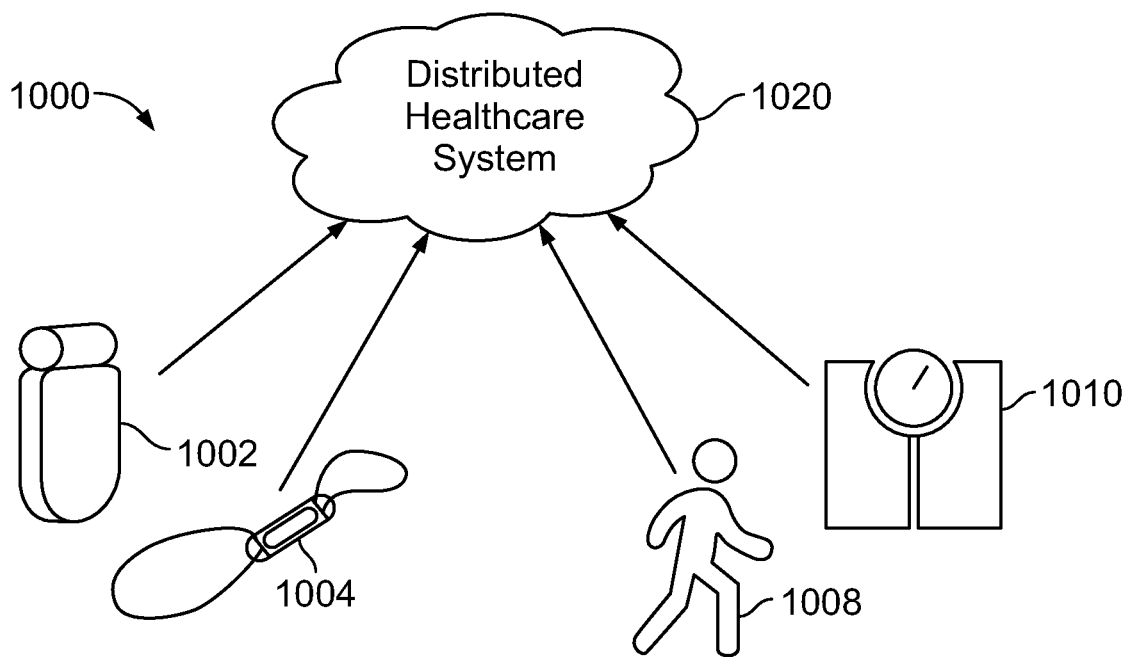
FIG. 10 illustrates a schematic diagram of a healthcare system in accordance with embodiments herein.

FIG. 10 illustrates a digital healthcare system implemented in accordance with embodiments herein. The system integrates accelerometer signals and the other information derived from accelerometer signals with other health data in connection with monitor a patient condition, progression of a health condition, trends in a patient's health condition, treatment, changes in therapy/medication and the like. The healthcare systems may include wearable PDE that communicate with an IMD or accelerometer and a remote database. As a result, the healthcare system may monitor health parameters of patient, including MD accelerometer data and TR parameters, and provide a diagnosis for the patient based on the monitored health parameters.

The system may be implemented with various architectures, that are collectively referred to as a healthcare system 1020. By way of example, the healthcare system 1020 may be implemented as described herein. The healthcare system 1020 is configured to receive data from a variety of external and implantable sources including, but not limited to, active IMDs 1002 capable of delivering therapy to a patient, passive IMDs or sensors 1004, wearable sensors 1008, and point-of-care (POC) devices 1010 (e.g., at home or at a medical facility). Any of the IMD 1002, sensor 1004, and/or sensor 1008 may implement an accelerometer circuity and perform the analysis of accelerometer signals as described herein. The data from one or more of the external and/or implantable sources is collected and communicated to one or more secure databases within the healthcare system 1020. Optionally, the patient and/or other users may utilize a PDE device, such as a smart phone, tablet device, etc., to enter data. For example, a patient may use a smart phone to provide feedback concerning activities performed by the patient, a patient diet, nutritional supplements and/or medications taken by the patient, how a patient is feeling (e.g., tired, dizzy, weak, good), etc.

CLOSING

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method, or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices, and program products according to various example embodiments. The program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system for verifying a cardiac related candidate pathologic episode of a patient, the system comprising:
   an accelerometer configured to be implanted in the patient, the accelerometer configured to obtain accelerometer data along at least one axis related to the patient;
   memory configured to store program instructions;
   one or more processors that, when executing the program instructions, are configured to:
   obtain a biological signal and identify a cardiac related candidate pathologic episode based on the biological signal;
   analyze the accelerometer data to identify a physical action experienced by the patient by comparing the accelerometer data related to the patient obtained before identification of the cardiac related candidate pathologic episode to the accelerometer data related to the patient obtained after the identification of the cardiac related candidate pathologic episode; and
   verify the cardiac related candidate pathologic episode based on the physical action.

2. The system of claim 1, wherein the physical action is activity of the patient or change in position of the patient.

3. The system of claim 1, wherein the one or more processors are further configured to deny the cardiac related candidate pathologic episode as a false episode when the physical action does not correspond to the cardiac related candidate pathologic episode.

4. The system of claim 1, wherein the biological signal corresponds to a cardiac activity signal, and the cardiac related candidate pathologic episode is at least one of a heart failure, stroke, syncope, arrythmia, heart attack, brady event, asystole, ventricular fibrillation, ventricular tachycardia, or seizure.

5. The system of claim 1, further comprising:
   a monitoring device configured to be implanted in the patient and in communication with the accelerometer, the monitoring device configured to:
   obtain the biological cardiac signal.

6. The system of claim 5, wherein the one or more processors are further configured to store the cardiac related candidate pathologic episode as an actual episode or a false episode based on the physical action analyzed.

7. The system of claim 5, wherein the monitoring device is further configured to wireless transmit, to an external device, at least one of the accelerometer data, or an alert signal.

8. The system of claim 1, wherein responsive to identifying the cardiac related candidate pathologic episode, the one or more processors obtains the accelerometer data related to the patient for an interval associated with the cardiac related candidate pathologic episode of the patient.

9. The system of claim 1, wherein the biological signal is an accelerometer signal, and the cardiac related candidate pathologic episode identified is a syncopal event.

10. The system of claim 1, wherein the one or more processors are further configured to:
    responsive to identifying the cardiac related candidate pathologic episode, obtain the accelerometer data for an interval associated with the cardiac related candidate pathologic episode; and wherein analyzing the accelerometer data includes analyzing the accelerometer data for the interval associated with the cardiac related candidate pathologic episode to identify the physical action experienced by the patient.

11. The system of claim 1, wherein the biological signal is obtained to identify the cardiac related candidate pathologic episode is received from an implantable medical device configured to monitor or treat a heart of the patient; and wherein the one or more processors analyze the accelerometer data to identify the physical action experienced by the patient by comparing the accelerometer data related to the patient obtained before identification of the candidate pathologic episode based on the biological signal from the implantable medical device to the accelerometer data related to the patient obtained after the identification of the candidate pathologic episode based on the biological signal from the implantable medical device.

12. A computer implemented method for verifying a cardiac related candidate pathologic episode of a patient, the method comprising:
    obtaining a biological signal and identifying the cardiac related candidate pathologic episode based on the biological signal;
    obtaining and analyzing accelerometer data related to a patient to identify a physical action experienced by the patient by comparing accelerometer data related to the patient obtained before identification of the cardiac related candidate pathologic episode to the accelerometer data related to the patient obtained after the detection of the cardiac related candidate pathologic episode; and verifying the cardiac related candidate pathologic episode based on the physical action.

13. The method of claim 12, further comprising denying the cardiac related candidate pathologic episode as a false episode when the physical action does not correspond to the cardiac related candidate pathologic episode.

14. The method of claim 12 further comprising wireless transmitting, to an external device, at least one of the accelerometer data, or an alert signal.

15. The method of claim 12, wherein responsive to identifying the cardiac related candidate pathologic episode, obtaining the accelerometer data related to the patient for an interval associated with the cardiac related candidate pathologic episode of the patient.

16. The method of claim 12, further comprising:
responsive to identifying the cardiac related candidate pathologic episode, obtaining the accelerometer data for an interval associated with the cardiac related candidate pathologic episode; and
wherein analyzing the accelerometer data includes analyzing the accelerometer data for the interval associated with the cardiac related candidate pathologic episode to identify the physical action experienced by the patient.

17. A system for verifying a syncopal event of a patient, the system comprising:
an accelerometer configured to be implanted in the patient, the accelerometer configured to obtain accelerometer data along at least one axis related to the patient;
memory configured to store program instructions;
one or more processors that, when executing the program instructions, are configured to:
identify the syncopal event based on a biological signal;
analyze the accelerometer data responsive to identifying the syncopal event to identify a physical action experienced by the patient by comparing the accelerometer data related to the patient obtained before identification of the syncopal event to the accelerometer data related to the patient obtained after the identification of the syncopal event; and
verify the syncopal event based on the physical action.

* * * * *